(12) United States Patent
Gilham et al.

(10) Patent No.: US 10,699,811 B2
(45) Date of Patent: Jun. 30, 2020

(54) METHODS AND SYSTEMS TO DETERMINE MULTI-PARAMETER MANAGED ALARM HIERARCHY DURING PATIENT MONITORING

(71) Applicant: Spacelabs Healthcare LLC, Snoqualmie, WA (US)

(72) Inventors: Jeffrey Jay Gilham, Sammamish, WA (US); William Gregory Downs, Snoqualmie, WA (US)

(73) Assignee: Spacelabs Healthcare L.L.C., Snoqualmie, WA (US)

( * ) Notice: Subject to any disclaimer, the term of this patent is extended or adjusted under 35 U.S.C. 154(b) by 265 days.

(21) Appl. No.: 15/463,250

(22) Filed: Mar. 20, 2017

(65) Prior Publication Data
US 2017/0281276 A1 Oct. 5, 2017

Related U.S. Application Data

(63) Continuation of application No. 13/045,539, filed on Mar. 11, 2011, now Pat. No. 9,629,566.

(51) Int. Cl.
*A61B 5/02* (2006.01)
*G16H 40/63* (2018.01)
(Continued)

(52) U.S. Cl.
CPC .............. *G16H 40/63* (2018.01); *A61B 5/02* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS 2,003,120 A 5/1935 Penniman
2,004,116 A 6/1935 Jennings
(Continued)

FOREIGN PATENT DOCUMENTS

CN 1293943 5/2001
CN 1348740 5/2002
(Continued)

OTHER PUBLICATIONS

"BleaseSirius Anesthesia Systems User Manual 1073-0212-00/ REV. B", Dec. 1, 2010, pp. 1-258, XP055209666.
(Continued)

*Primary Examiner* — Erica S Lee
(74) *Attorney, Agent, or Firm* — Novel IP

(57) ABSTRACT

The present specification discloses systems and methods of patient monitoring in which multiple sensors are used to detect physiological parameters and the data from those sensors are correlated to determine if an alarm should, or should not, be issued, thereby resulting in more precise alarms and fewer false alarms. Electrocardiogram readings can be combined with invasive blood pressure, non-invasive blood pressure, and/or pulse oximetry measurements to provide a more accurate picture of pulse activity and patient respiration. In addition, the monitoring system can also use an accelerometer or heart valve auscultation to further improve accuracy.

24 Claims, 10 Drawing Sheets

(51) Int. Cl.

| | | |
|---|---|---|
| *A61B 5/00* | (2006.01) | |
| *A61B 5/0205* | (2006.01) | |
| *A61B 5/021* | (2006.01) | |
| *A61B 5/0245* | (2006.01) | |
| *A61B 5/0468* | (2006.01) | |
| *A61B 5/113* | (2006.01) | |
| *A61B 5/145* | (2006.01) | |
| *A61B 5/0402* | (2006.01) | |
| *G08B 25/01* | (2006.01) | |
| *A61B 5/083* | (2006.01) | |

(52) U.S. Cl.
CPC ........ *A61B 5/02455* (2013.01); *A61B 5/0402* (2013.01); *A61B 5/0468* (2013.01); *A61B 5/1135* (2013.01); *A61B 5/14542* (2013.01); *A61B 5/7246* (2013.01); *G08B 25/016* (2013.01); *A61B 5/0836* (2013.01)

(56) References Cited

U.S. PATENT DOCUMENTS

| | | |
|---|---|---|
| 2,005,005 A | 6/1935 | Preston |
| 2,005,146 A | 6/1935 | Kotrbaty |
| 2,006,213 A | 6/1935 | Halliday |
| 2,007,120 A | 7/1935 | Holmes |
| 2,008,221 A | 7/1935 | Molander |
| 2,008,251 A | 7/1935 | Hillebrand |
| 2,009,121 A | 7/1935 | Price |
| 2,009,326 A | 7/1935 | Sanchez-Vello |
| 2,246,464 A | 6/1941 | Gerber |
| 2,808,580 A | 10/1957 | Fuller |
| 2,820,651 A | 1/1958 | Phillips |
| 2,912,858 A | 11/1959 | Fuller |
| 2,944,547 A | 7/1960 | Ziherl |
| 3,517,639 A | 6/1970 | Whitsel |
| 3,608,545 A | 9/1971 | Novack |
| 3,618,592 A | 11/1971 | Stewart |
| 3,673,863 A | 7/1972 | Spacek |
| 3,689,908 A | 9/1972 | Ray |
| 3,733,482 A | 5/1973 | Miller |
| 3,757,577 A | 9/1973 | Bozek |
| 3,844,171 A | 10/1974 | Rodger |
| 3,897,606 A | 8/1975 | Schleining |
| 3,938,551 A | 2/1976 | Henkin |
| 3,954,010 A | 5/1976 | Hilblom |
| 3,981,329 A | 9/1976 | Wohlwend |
| 4,064,826 A | 12/1977 | Pauli |
| 4,148,312 A | 4/1979 | Bird |
| 4,167,115 A | 9/1979 | Stoever |
| 4,428,230 A | 1/1984 | Testone |
| 4,428,507 A | 1/1984 | Sneider |
| 4,513,294 A | 4/1985 | Anderson |
| 4,557,216 A | 12/1985 | Demyon |
| 4,615,547 A | 10/1986 | Sutcliffe |
| 4,625,731 A | 12/1986 | Quedens |
| 4,630,485 A | 12/1986 | Wastl, Sr. |
| 4,630,486 A | 12/1986 | Miles |
| 4,643,693 A | 2/1987 | Rubinstein |
| 4,697,450 A | 10/1987 | Bachman |
| 4,869,253 A | 9/1989 | Craig |
| 4,879,997 A | 11/1989 | Bickford |
| 4,899,585 A | 2/1990 | Kulha |
| 4,903,222 A | 2/1990 | Carter |
| 4,944,305 A | 7/1990 | Takatsu |
| 4,989,791 A | 2/1991 | Ridenour |
| 4,991,576 A | 2/1991 | Henkin |
| 4,993,683 A | 2/1991 | Kreuzer |
| 5,087,906 A | 2/1992 | Eaton |
| 5,101,851 A | 4/1992 | Abadi |
| 5,144,898 A | 9/1992 | Posly |
| 5,174,163 A | 12/1992 | Gussman |
| 5,197,480 A | 3/1993 | Gebhardt |
| 5,213,108 A | 5/1993 | Bredesen |
| 5,222,486 A | 6/1993 | Vaughn |
| 5,231,981 A | 8/1993 | Schreiber |
| 5,233,975 A | 8/1993 | Choate |
| 5,253,641 A | 10/1993 | Choate |
| 5,262,944 A | 11/1993 | Weisner |
| 5,291,182 A | 3/1994 | Wiseman |
| 5,292,564 A | 3/1994 | Lee |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,333,106 A | 7/1994 | Lanpher |
| 5,339,826 A | 8/1994 | Schmidt |
| 5,348,008 A | 9/1994 | Bomn |
| 5,372,389 A | 12/1994 | Tam |
| 5,373,746 A | 12/1994 | Bloss |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,520,191 A | 5/1996 | Karlsson |
| 5,553,296 A | 9/1996 | Forrest |
| 5,558,418 A | 9/1996 | Lambright |
| 5,563,495 A | 10/1996 | Tomiyori |
| 5,584,291 A | 12/1996 | Vapola |
| 5,586,909 A | 12/1996 | Saba |
| 5,633,457 A | 5/1997 | Kilar |
| 5,682,526 A | 10/1997 | Smokoff |
| 5,684,504 A | 11/1997 | Verhulst |
| 5,687,717 A | 11/1997 | Halpern |
| 5,692,494 A | 12/1997 | Pernetti |
| 5,715,813 A | 2/1998 | Guevrekian |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,752,917 A | 5/1998 | Fuchs |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,800,387 A | 9/1998 | Duffy |
| 5,819,741 A | 10/1998 | Karlsson |
| 5,855,550 A | 1/1999 | Lai |
| 5,868,133 A | 2/1999 | DeVries |
| 5,904,328 A | 5/1999 | Leveridge |
| 5,956,013 A | 9/1999 | Raj |
| 5,966,760 A | 10/1999 | Gallant |
| 5,975,081 A | 11/1999 | Hood |
| 6,005,767 A | 12/1999 | Ku |
| 6,008,809 A | 12/1999 | Brooks |
| 6,024,089 A | 2/2000 | Wallace |
| 6,042,548 A | 3/2000 | Giuffre |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,167,401 A | 12/2000 | Csipkes |
| 6,188,407 B1 | 2/2001 | Smith |
| 6,221,012 B1 | 4/2001 | Maschke |
| 6,269,813 B1 | 8/2001 | Fitzgerald |
| 6,322,502 B1 | 11/2001 | Schoenberg |
| 6,338,823 B1 | 1/2002 | Furukawa |
| 6,339,732 B1 | 1/2002 | Phoon |
| 6,347,310 B1 | 2/2002 | Passera |
| 6,349,436 B1 | 2/2002 | Kreuzer |
| 6,364,834 B1 | 4/2002 | Reuss |
| 6,383,136 B1 | 5/2002 | Jordan |
| 6,396,583 B1 | 5/2002 | Clare |
| 6,416,471 B1 | 7/2002 | Kumar |
| 6,424,860 B1 | 7/2002 | Karlsson |

(56) References Cited

U.S. PATENT DOCUMENTS

| | | |
|---|---|---|
| 6,435,690 B1 | 8/2002 | Till |
| 6,443,889 B1 | 9/2002 | Groth |
| D467,001 S | 12/2002 | Buczek |
| 6,488,029 B1 | 12/2002 | Hood |
| 6,536,430 B1 | 3/2003 | Smith |
| 6,541,758 B2 | 4/2003 | Yashiro |
| 6,554,238 B1 | 4/2003 | Hibberd |
| 6,571,227 B1 | 5/2003 | Agrafiotis |
| 6,571,792 B1 | 6/2003 | Hendrickson |
| 6,591,694 B2 | 7/2003 | Tsai |
| 6,600,662 B1 | 7/2003 | Emmert |
| 6,647,341 B1 | 11/2003 | Golub |
| 6,650,779 B2 | 11/2003 | Vachtesvanos |
| 6,674,837 B1 | 1/2004 | Taskar |
| 6,692,258 B1 | 2/2004 | Kurzweil |
| 6,692,436 B1 | 2/2004 | Bluth |
| 6,699,187 B2 | 3/2004 | Webb |
| 6,702,754 B2 | 3/2004 | Ogura |
| 6,715,722 B2 | 4/2004 | Roberts |
| 6,735,648 B2 | 5/2004 | Onishi |
| 6,771,172 B1 | 8/2004 | Robinson |
| 6,790,178 B1 | 9/2004 | Mault |
| 6,796,264 B1 | 9/2004 | Appenzeller |
| 6,804,656 B1 | 10/2004 | Rosenfeld |
| 6,824,539 B2 | 11/2004 | Novak |
| 6,829,501 B2 | 12/2004 | Nielsen |
| 6,868,495 B1 | 3/2005 | Glover |
| 6,896,241 B2 | 5/2005 | Chen |
| 6,931,795 B1 | 8/2005 | Baloga |
| 6,933,931 B2 | 8/2005 | Lubarsky, Jr. |
| 6,985,762 B2 | 1/2006 | Brashears |
| 7,006,865 B1 | 2/2006 | Cohen |
| 7,013,833 B2 | 3/2006 | Lemberger |
| 7,024,569 B1 | 4/2006 | Wright |
| 7,031,857 B2 | 4/2006 | Tarassenko |
| 7,038,588 B2 | 5/2006 | Boone |
| 7,040,175 B1 | 5/2006 | Huang |
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,128,709 B2 | 10/2006 | Saruya |
| 7,137,951 B2 | 11/2006 | Pilarski |
| 7,193,233 B2 | 3/2007 | Smith |
| 7,216,802 B1 | 5/2007 | De La Huerga |
| 7,219,559 B2 | 5/2007 | Sugi |
| 7,223,007 B1 | 5/2007 | Fredley |
| 7,234,944 B2 | 6/2007 | Nordin |
| 7,256,708 B2 | 9/2007 | Rosenfeld |
| 7,265,676 B2 | 9/2007 | Gordon |
| 7,267,666 B1 | 9/2007 | Duchon |
| 7,282,029 B1 | 10/2007 | Poulsen |
| 7,310,544 B2 | 12/2007 | Brister |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,468,032 B2 | 12/2008 | Stahmann |
| 7,469,601 B2 | 12/2008 | Sugi |
| 7,489,250 B2 | 2/2009 | Bock |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,530,949 B2 | 5/2009 | AlAli |
| 7,540,187 B1 | 6/2009 | Dillon |
| 7,566,307 B2 | 7/2009 | Inukai |
| 7,621,500 B2 | 11/2009 | Ishizaki |
| 7,704,212 B2 | 4/2010 | Wekell |
| 7,710,567 B1 | 5/2010 | Mentzer |
| 7,751,878 B1 | 7/2010 | Merkle |
| 7,756,722 B2 | 7/2010 | Levine |
| 7,836,882 B1 | 11/2010 | Rumph |
| 7,945,452 B2 | 5/2011 | Fathallah |
| 7,974,924 B2 | 7/2011 | Holla |
| 8,002,701 B2 | 8/2011 | John |
| 8,027,846 B2 | 9/2011 | Schoenberg |
| 8,033,686 B2 | 10/2011 | Recker |
| 8,091,422 B2 | 1/2012 | Felske |
| 8,147,419 B2 | 4/2012 | Krauss |
| 8,190,900 B2 | 5/2012 | Corndorf |
| 8,233,272 B2 | 7/2012 | Fidacaro |
| 8,273,018 B1 | 9/2012 | Fackler |
| 8,344,847 B2 | 1/2013 | Moberg |
| 8,398,408 B1 | 3/2013 | Hansen |
| 8,413,271 B2 | 4/2013 | Blanchard |
| 8,544,406 B2 | 10/2013 | Fujihira |
| 8,593,275 B2 | 11/2013 | Davis |
| 8,704,666 B2 | 4/2014 | Baker, Jr. |
| 8,798,527 B2 | 8/2014 | Gaines |
| 8,811,888 B2 | 8/2014 | Wiesner |
| 8,818,260 B2 | 8/2014 | Gaines |
| 8,855,550 B2 | 10/2014 | Gaines |
| 8,868,028 B1 | 10/2014 | Kaltsukis |
| 8,897,198 B2 | 11/2014 | Gaines |
| 8,903,308 B2 | 12/2014 | Wiesner |
| 8,922,330 B2 | 12/2014 | Moberg |
| 8,931,702 B2 | 1/2015 | Wekell |
| 8,940,147 B1 | 1/2015 | Bartsch |
| 8,943,168 B2 | 1/2015 | Wiesner |
| 9,020,419 B2 | 4/2015 | Gaines |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0013517 A1 | 1/2002 | West |
| 2002/0026941 A1 | 3/2002 | Biondi |
| 2002/0032386 A1 | 3/2002 | Sackner |
| 2002/0060247 A1 | 5/2002 | Krishnaswamy |
| 2002/0095424 A1 | 7/2002 | Chung |
| 2002/0108011 A1 | 8/2002 | Tanha |
| 2002/0138017 A1 | 9/2002 | Bui |
| 2002/0161291 A1 | 10/2002 | Kianl |
| 2002/0173991 A1 | 11/2002 | Avitall |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0144699 A1 | 7/2003 | Freeman |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0149892 A1 | 8/2004 | Akitt |

(56) References Cited

U.S. PATENT DOCUMENTS

| | | |
|---|---|---|
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | Necola Shehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0113704 A1 | 5/2005 | Lawson |
| 2005/0124866 A1 | 6/2005 | Elaz |
| 2005/0139213 A1 | 6/2005 | Blike |
| 2005/0146431 A1 | 7/2005 | Hastings |
| 2005/0148890 A1 | 7/2005 | Hastings |
| 2005/0151640 A1 | 7/2005 | Hastings |
| 2005/0177096 A1 | 8/2005 | Bollish |
| 2005/0192845 A1 | 9/2005 | Brinsfield |
| 2005/0229110 A1 | 10/2005 | Gegner |
| 2005/0251232 A1 | 11/2005 | Hartley |
| 2006/0004475 A1 | 1/2006 | Brackett |
| 2006/0013462 A1 | 1/2006 | Sadikali |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0161295 A1 | 7/2006 | Yun |
| 2006/0199618 A1 | 9/2006 | Steer |
| 2006/0226992 A1 | 10/2006 | Al-Ali |
| 2006/0258926 A1 | 11/2006 | Ali |
| 2006/0278270 A1 | 12/2006 | Jones |
| 2006/0280621 A1 | 12/2006 | Kinugawa |
| 2006/0282302 A1 | 12/2006 | Hussain |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0050715 A1 | 3/2007 | Behar |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | DePaepe |
| 2007/0176931 A1 | 8/2007 | Tivig |
| 2007/0180140 A1 | 8/2007 | Welch |
| 2007/0199388 A1 | 8/2007 | Furkert |
| 2007/0199566 A1 | 8/2007 | Be |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0077435 A1 | 3/2008 | Muradia |
| 2008/0103375 A1 | 5/2008 | Kiani |
| 2008/0117029 A1 | 5/2008 | Dohrmann |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0221418 A1 | 9/2008 | Al-Ali |
| 2008/0221495 A1 | 9/2008 | Steffens |
| 2008/0228045 A1 | 9/2008 | Gao |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005651 A1 | 1/2009 | Ward |
| 2009/0005703 A1 | 1/2009 | Fasciano |
| 2009/0015116 A1 | 1/2009 | Arceta |
| 2009/0024008 A1 | 1/2009 | Brunner |
| 2009/0043171 A1 | 2/2009 | Rule |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0076397 A1* | 3/2009 | Libbus ............... A61B 5/04087 600/484 |
| 2009/0099480 A1 | 4/2009 | Salgo |
| 2009/0117784 A1 | 5/2009 | Wu |
| 2009/0124239 A1 | 5/2009 | Tsuei |
| 2009/0131805 A1 | 5/2009 | OBrien |
| 2009/0133609 A1 | 5/2009 | Nethken |
| 2009/0149901 A1 | 6/2009 | Jayne |
| 2009/0151720 A1 | 6/2009 | Inoue |
| 2009/0182204 A1 | 7/2009 | Semler |
| 2009/0190713 A1* | 7/2009 | Wai .................... A61B 5/02438 377/24.2 |
| 2009/0192541 A1 | 7/2009 | Ortiz |
| 2009/0193315 A1 | 7/2009 | Gower |
| 2009/0200902 A1 | 8/2009 | McKay |
| 2009/0206713 A1 | 8/2009 | Vilkas |
| 2009/0209849 A1 | 8/2009 | Rowe |
| 2009/0213034 A1 | 8/2009 | Wu |
| 2009/0237264 A1 | 9/2009 | Bobey |
| 2009/0326340 A1 | 12/2009 | Wang |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0056877 A1 | 3/2010 | Fein |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1 | 6/2010 | Pierry |
| 2010/0156655 A1 | 6/2010 | Bullemer |
| 2010/0164452 A1 | 7/2010 | Ruan |
| 2010/0175695 A1 | 7/2010 | Jamison |
| 2010/0179400 A1 | 7/2010 | Brauker |
| 2010/0198027 A1 | 8/2010 | Dixon |
| 2010/0233891 A1 | 9/2010 | Broeksteeg |
| 2010/0238138 A1 | 9/2010 | Goertz |
| 2010/0259881 A1 | 10/2010 | Choi |
| 2010/0261979 A1 | 10/2010 | Kiani |
| 2010/0282256 A1 | 11/2010 | Loescher |
| 2010/0285771 A1 | 11/2010 | Peabody |
| 2010/0294405 A1 | 11/2010 | Longinotti-Buitoni |
| 2010/0298655 A1* | 11/2010 | McCombie .......... A61B 5/0002 600/301 |
| 2010/0298656 A1 | 11/2010 | McCombie |
| 2010/0298718 A1 | 11/2010 | Gilham |
| 2010/0318578 A1 | 12/2010 | Treu |
| 2010/0324380 A1 | 12/2010 | Perkins |
| 2010/0324384 A1 | 12/2010 | Moon |
| 2010/0324936 A1 | 12/2010 | Vishnubhatla |
| 2011/0004071 A1 | 1/2011 | Faiola |
| 2011/0006876 A1 | 1/2011 | Moberg |
| 2011/0015493 A1 | 1/2011 | Koschek |

(56) References Cited

U.S. PATENT DOCUMENTS

| | | |
|---|---|---|
| 2011/0055205 A1 | 3/2011 | Scott |
| 2011/0071420 A1 | 3/2011 | Pierre |
| 2011/0077971 A1 | 3/2011 | Surwit |
| 2011/0087756 A1 | 4/2011 | Biondi |
| 2011/0088694 A1 | 4/2011 | Tobia |
| 2011/0125040 A1 | 5/2011 | Crawford |
| 2011/0130798 A1 | 6/2011 | Elghazzawi |
| 2011/0138323 A1 | 6/2011 | Skidmore |
| 2011/0152629 A1 | 6/2011 | Eaton |
| 2011/0164074 A1 | 7/2011 | Frank |
| 2011/0190643 A1 | 8/2011 | Zhang |
| 2011/0224531 A1 | 9/2011 | Steiner |
| 2011/0225771 A1 | 9/2011 | Bartnick |
| 2011/0227739 A1 | 9/2011 | Gilham |
| 2011/0245579 A1 | 10/2011 | Bruggeman |
| 2011/0245688 A1* | 10/2011 | Arora ............... A61B 5/0205 600/483 |
| 2011/0257489 A1 | 10/2011 | Banet |
| 2011/0270058 A1* | 11/2011 | Price ............... A61B 5/021 600/324 |
| 2011/0279383 A1 | 11/2011 | Wilson |
| 2011/0279958 A1 | 11/2011 | Clark |
| 2011/0298718 A1 | 12/2011 | Chang |
| 2012/0030610 A1 | 2/2012 | DiPerna |
| 2012/0041783 A1 | 2/2012 | McKee |
| 2012/0041786 A1 | 2/2012 | Yu |
| 2012/0075060 A1 | 3/2012 | Connor |
| 2012/0075327 A1 | 3/2012 | Mackenzie |
| 2012/0093311 A1 | 4/2012 | Nierzwick |
| 2012/0095778 A1 | 4/2012 | Gross |
| 2012/0101396 A1* | 4/2012 | Solosko ............... A61B 5/0006 600/509 |
| 2012/0105233 A1 | 5/2012 | Bobey |
| 2012/0105774 A1 | 5/2012 | Fletcher |
| 2012/0108991 A1* | 5/2012 | Song ............... A61B 5/0245 600/509 |
| 2012/0116331 A1 | 5/2012 | Locke |
| 2012/0127103 A1 | 5/2012 | Qualey |
| 2012/0136231 A1 | 5/2012 | Markel |
| 2012/0180789 A1 | 7/2012 | Tobia |
| 2012/0184120 A1 | 7/2012 | Basta |
| 2012/0203491 A1* | 8/2012 | Sun ............... A61B 5/0006 702/108 |
| 2012/0209984 A1 | 8/2012 | Gonzalez-Banos |
| 2012/0232398 A1 | 9/2012 | Roham |
| 2012/0233679 A1 | 9/2012 | Shedrinsky |
| 2012/0245439 A1 | 9/2012 | Andre |
| 2012/0330675 A1 | 12/2012 | Muradia |
| 2013/0015966 A1 | 1/2013 | Soomro |
| 2013/0030258 A1* | 1/2013 | Cheung ............... G06F 19/3418 600/301 |
| 2013/0107445 A1 | 5/2013 | Reber |
| 2013/0162426 A1 | 6/2013 | Wiesner |
| 2013/0267861 A1 | 10/2013 | Vassallo |
| 2014/0142963 A1 | 5/2014 | Hill |
| 2014/0153747 A1 | 6/2014 | Contolini |
| 2014/0275873 A1 | 9/2014 | Fries |
| 2015/0018703 A1 | 1/2015 | Shetty |
| 2016/0120445 A1* | 5/2016 | Peluso ............... A61B 5/1112 600/301 |

FOREIGN PATENT DOCUMENTS

| | | |
|---|---|---|
| CN | 1593764 A | 3/2005 |
| CN | 1688256 | 10/2005 |
| CN | 1781107 A | 5/2006 |
| CN | 1943505 A | 4/2007 |
| CN | 1983258 A | 6/2007 |
| CN | 101194278 | 6/2008 |
| CN | 101496923 | 8/2009 |
| CN | 101501683 | 8/2009 |
| CN | 101521845 | 9/2009 |
| CN | 101611410 | 12/2009 |
| CN | 201570216 U | 9/2010 |
| CN | 201594642 U | 9/2010 |
| CN | 101893916 | 11/2010 |
| CN | 102184312 | 9/2011 |
| CN | 102567624 | 7/2012 |
| DE | 9415672 | 11/1994 |
| DE | 102006011151 | 9/2007 |
| EP | 0596509 | 5/1994 |
| EP | 068900 A2 | 12/1995 |
| EP | 0686900 | 12/1995 |
| EP | 0955007 A1 | 11/1999 |
| EP | 1054338 | 11/2000 |
| EP | 1227752 A1 | 5/2001 |
| EP | 1449558 | 8/2004 |
| EP | 1852060 | 11/2007 |
| EP | 1868123 A1 | 12/2007 |
| EP | 1197178 | 7/2008 |
| EP | 2555668 A2 | 2/2013 |
| EP | 2641151 | 9/2013 |
| EP | 2651482 | 10/2013 |
| EP | 2709518 | 3/2014 |
| EP | 2805564 A4 | 9/2015 |
| GB | 191214095 | 10/1912 |
| GB | 568212 | 3/1945 |
| GB | 2389290 A | 12/2003 |
| JP | 13286735 | 12/1991 |
| JP | 05143611 | 6/1993 |
| JP | 15184550 | 7/1993 |
| JP | 15341771 | 12/1993 |
| JP | 07163527 | 6/1995 |
| JP | 08504345 | 5/1996 |
| JP | 08504531 | 5/1996 |
| JP | 08275926 | 10/1996 |
| JP | 19108194 | 4/1997 |
| JP | 2003210422 | 7/2003 |
| JP | 2005529396 | 9/2005 |
| JP | 2008532587 | 8/2008 |
| JP | 2009054381 | 3/2009 |
| JP | 2009211589 | 9/2009 |
| JP | 2009245435 | 10/2009 |
| JP | 2010086535 | 4/2010 |
| JP | 2011078640 | 4/2011 |
| WO | 9415523 A1 | 7/1994 |
| WO | 1994015523 | 7/1994 |
| WO | 1999018705 | 4/1999 |
| WO | 1999027326 | 6/1999 |
| WO | 2000042911 | 7/2000 |
| WO | 03091841 | 11/2003 |
| WO | 03102850 | 12/2003 |
| WO | 2004038669 A1 | 5/2004 |
| WO | 2005101276 A3 | 10/2005 |
| WO | 2005114524 A3 | 12/2005 |
| WO | 2006090371 | 8/2006 |
| WO | 2006094055 A2 | 9/2006 |
| WO | 2010126797 | 11/2010 |
| WO | 2010126916 | 11/2010 |
| WO | 2010126916 A1 | 11/2010 |
| WO | 2011001302 | 1/2011 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |

(56) References Cited

FOREIGN PATENT DOCUMENTS

| WO | 2014055660 A1 | 4/2014 |
|---|---|---|
| WO | 2014194193 | 12/2014 |

OTHER PUBLICATIONS

"Lifegard II Patient Monitor Operator's Manual", Jan. 1, 2006, pp. 1-1, XP055209485.
Chinese Office Action, Patent Application No. 201180025170X, dated Apr. 21, 2014, First OA.
European Search Report for EP12786443.7, dated Apr. 15, 2015.
Extended European Search Report, EP 11861868.5, dated Sep. 28, 2015.
Extended European Search Report for EP12839321, dated Dec. 1, 2015.
First Office Action, Chinese Patent Application No. 201180067543.X, dated Jun. 2014.
First Office Action, Chinese Patent Application No. 2012800351488, dated Jun. 13, 2015.
Google patents search, Sep. 25, 2015, U.S. Appl. No. 14/044,524.
IntelliVue Patient Monitor; MP20/30, MP40/50, MP60/70/80/90, Release G.0 with Software Revision G.0x.xx (Philips) Sep. 2008; pp. 4, 10, 19, 20, 46-49, 82, 326, 348, 420, 422, 424, 452; Accessed on Sep. 30, 2013: <http://www.mc.vanderbilt.edu/documents/nursingeducationresources/files/MP20-MP90%20Instructions%20for%20Use%20Manual%20Rev_G_0%20%20English%20M8000-9001K.pdf>.
International Preliminary Report on Patentability, PCT/US12/38000, dated Nov. 13, 2013.
International Preliminary Report on Patentability, PCT/US2006/007269, dated Sep. 11, 2007, Spacelabs Medical.
International Preliminary Report on Patentability, PCT/US2011/028007, dated Sep. 17, 2013, International Search Authority.
International Preliminary Report on Patentability, PCT/US2011/065678, dated Jun. 18, 2013, International Search Authority.
International Preliminary Report on Patentability, PCT/US2011/065685, dated Jun. 18, 2013.
International Preliminary Report on Patentability for PCT/US2011/061554, dated Feb. 25, 2014.
International Search Report, PCT/US2011/028007, dated Jul. 11, 2011, International Search Authority.
International Search Report, PCT/US2011/065685, dated May 8, 2012, International Search Authority.
International Search Report for PCT/US06/07269, dated Aug. 28, 2006.
International Search Report for PCT/US10/32635, dated Jul. 23, 2010.
International Search Report for PCT/US10/34025, dated Aug. 9, 2010.
International Search Report for PCT/US12/38000, dated Oct. 23, 2012.
International Search Report for PCT/US2010/052977, dated Mar. 18, 2011.
International Search Report for PCT/US2011/029278, dated Aug. 2, 2011.
International Search Report for PCT/US2011/061554, dated Feb. 14, 2014.
International Search Report for PCT/US2011/061555, dated Apr. 17, 2012.
International Search Report for PCT/US2011/061558, dated Aug. 10, 2012.
International Search Report for PCT/US2011/065676, dated Sep. 20, 2012.
International Search Report for PCT/US2011/065678, dated Jun. 29, 2012.
International Search Report for PCT/US2011/61557, dated Apr. 23, 2012.
International Search Report for PCT/US2012/060125, dated Apr. 19, 2013.
International Search Report for PCT/US2013/041246, dated Dec. 9, 2013.
International Search Report for PCT/US2013/041247, dated Jan. 10, 2014.
International Search Report for PCT/US2013/063087, dated Mar. 6, 2014.
International Search Report for PCT/US2014/040225, dated Nov. 5, 2014.
Notice of Allowance dated Jan. 28, 2015 for U.S. Appl. No. 13/300,478.
Notice of Allowance dated Jan. 8, 2015 for U.S. Appl. No. 13/329,259.
Notice of Allowance dated Mar. 13, 2015 for U.S. Appl. No. 12/906,081.
Notice of Allowance dated May 11, 2015 for U.S. Appl. No. 13/300,462.
Notice of Allowance dated May 27, 2015 for U.S. Appl. No. 14/165,193.
Notice of Allowance dated Nov. 18, 2015 for U.S. Appl. No. 14/557,135.
Notice of Allowance dated Oct. 31, 2014 for U.S. Appl. No. 12/114,689.
Notice of Allowance dated Sep. 3, 2014 for U.S. Appl. No. 13/973,862.
Office Action dated Apr. 16, 2015 for U.S. Appl. No. 14/557,135.
Office Action dated Apr. 24, 2015 for U.S. Appl. No. 13/651,337.
Office Action dated Apr. 7, 2015 for U.S. Appl. No. 13/472,332.
Office Action dated Aug. 1, 2011 for U.S. Appl. No. 11/716,513.
Office Action dated Aug. 14, 2014 for U.S. Appl. No. 12/768,714.
Office Action dated Aug. 28, 2009 for U.S. Appl. No. 11/716,513.
Office Action dated Aug. 4, 2015 for U.S. Appl. No. 13/329,219.
Office Action dated Aug. 6, 2015 for U.S. Appl. No. 13/045,539.
Office Action dated Dec. 10, 2014 for U.S. Appl. No. 14/165,193.
Office Action dated Feb. 10, 2016 for U.S. Appl. No. 13/895,270.
Office Action dated Feb. 11, 2016 for U.S. Appl. No. 13/895,281.
Office Action dated Feb. 26, 2015 for U.S. Appl. No. 12/768,714.
Office Action dated Feb. 9, 2016 for U.S. Appl. No. 13/045,539.
Office Action dated Jan. 15, 2016 for U.S. Appl. No. 14/312,566.
Office Action dated Jan. 17, 2013 for U.S. Appl. No. 12/768,714.
Office Action dated Jan. 20, 2016 for U.S. Appl. No. 13/651,337.
Office Action dated Jul. 2, 2012 for U.S. Appl. No. 11/716,513.
Office Action dated Jul. 2, 2015 for U.S. Appl. No. 13/895,527.
Office Action dated Jun. 18, 2012 for U.S. Appl. No. 12/768,714.
Office Action dated Jun. 18, 2015 for U.S. Appl. No. 13/329,186.
Office Action dated Mar. 23, 2010 for U.S. Appl. No. 11/716,513.
Office Action dated May 21, 2015 for U.S. Appl. No. 13/300,526.
Office Action dated May 31, 2013 for U.S. Appl. No. 13/052,883.
Office Action dated Nov. 12, 2014 for U.S. Appl. No. 13/300,462.
Office Action dated Nov. 13, 2015 for U.S. Appl. No. 13/472,332.
Office Action dated Nov. 21, 2013 for U.S. Appl. No. 12/768,714.
Office Action dated Nov. 21, 2014 for U.S. Appl. No. 13/045,539.
Office Action dated Oct. 14, 2015 for U.S. Appl. No. 14/460,147.
Office Action dated Oct. 2, 2015 for U.S. Appl. No. 14/044,524.
Office Action dated Oct. 7, 2015 for U.S. Appl. No. 12/768,714.
Office Action dated Sep. 22, 2014 for U.S. Appl. No. 13/329,186.
Office Action for Chinese Patent Application No. 201080057413.3, dated Oct. 10, 2015.
Office Action for Chinese Patent Application No. 2011800655173, dated May 15, 2015.
Office Action for Chinese Patent Application No. 2011800707731, dated Sep. 29, 2015.
Office Action dated Jan. 6, 2016 for U.S. Appl. No. 13/329,219.
Partial European Search Report for EP 12839321.2, dated May 26, 2015.
Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
Second Office Action, Chinese Patent Application No. 201180025170X, dated Jun. 7, 2015.
Second Office Action for Chinese Patent Application No. 201180067543.X, dated Nov. 11, 2015.

(56) References Cited

OTHER PUBLICATIONS

Supplemental Notice of Allowance dated Apr. 20, 2015 for U.S. Appl. No. 12/906,081.
Supplementary European Search Report, dated Nov. 25, 2009, Spacelabs Medical, PCT/US2006/007269.
Third Office Action, Chinese Patent Application No. 201180025170X, dated Dec. 10, 2015.
Examination Report for GB12169124, dated Dec. 2, 2015.
First Office Action for Chinese Patent Application No. CN2011800653708, dated Feb. 3, 2016.
Notice of Allowance dated Mar. 2, 2016 for U.S. Appl. No. 14/460,147.
Notice of Allowance dated May 20, 2016 for U.S. Appl. No. 14/312,566.
Office Action dated Apr. 1, 2016 for U.S. Appl. No. 13/329,186.
Office Action dated May 9, 2016 for U.S. Appl. No. 13/472,332.
Office Action for Mexican Patent Application No. 2014013947, dated Feb. 26, 2016.
Supplementary European Search Report for EP13790605, completed on Feb. 29, 2016.
Office Action dated Jul. 12, 2016 for U.S. Appl. No. 14/044,524.
Second Office Action, Chinese Patent Application No. 2012800351488, dated Dec. 10, 2015.
First Office Action for CN2011800655972, dated Nov. 5, 2015.
Office Action dated Jul. 14, 2016 for U.S. Appl. No. 13/329,186.
Second Office Action for Mexican Patent Application No. 2014013947, dated Jul. 28, 2016.
Supplementary Partial European Search Report for EP13790154, completed on Feb. 11, 2016.
Philips: 'IntelliVue Patient Monitor; MP20/30, MP40/50, MP60/70/80/90', Internet Citation, Sep. 1, 2008, pp. 2PP, I-X, 1, XP003034216.
Anonymous: 'Docking station-wikipedia, the free encyclopedia', Feb. 20, 2012, XP055284610.
Anonymous: 'Pogo pin-wikipedia, the free encyclopedia', Apr. 28, 2012, XP055284974.
Supplementary European Search Report for EP13790154, completed on Jul. 1, 2016.
First Office Action for CN201380037855.5, dated Dec. 21, 2015.
Office Action for CN201380060910.2, dated Jul. 13, 2016.
Examination Report for GB1321385.5, dated Mar. 31, 2016.
Office Action dated Sep. 15, 2016 for U.S. Appl. No. 13/895,270.
Office Action dated Nov. 9, 2016 for U.S. Appl. No. 13/472,332.
Notice of Allowance dated Nov. 7, 2016 for U.S. Appl. No. 13/651,337.
Examination Report for GB12169124, dated Apr. 21, 2016.
Examination Report for GB12169124, dated Feb. 15, 2016.
Examination Report for GB13108402, dated Sep. 30, 2016.
Examination Report for GB13108402, dated Nov. 3, 2016.
Second Office Action for CN2011800655972, dated May 24, 2016.
Office Action dated Dec. 9, 2016 for U.S. Appl. No. 12/768,714.
Notice of Allowance dated Dec. 22, 2016 for U.S. Appl. No. 13/045,539.
Anonymous: "Routing table", Wikipedia, Oct. 3, 2012 (Oct. 3, 2012), XP055321398, Retrieved from the Internet: URL: https://en.wikipedia.org/w/index.php?title=Routing_table&oldid=515747820, [retrieved on Nov. 21, 2016].
Anonymous: "Metrics (networking)", Wikipedia, Jul. 18, 2012 (Jul. 18, 2012), XP055321558, Retrieved from the Internet: URL: https://en.wikipedia.org/w/index.php?title=Metrics_(networking)&oldid=502970743, [retrieved on Nov. 22, 2016].
Supplementary European Search Report for EP13843278, completed on Nov. 22, 2016.
Office Action dated Jan. 25, 2017 for U.S. Appl. No. 13/895,270.
Office Action dated Mar. 9, 2017 for U.S. Appl. No. 13/895,281.
Examination Report for GB1321385.5, dated Aug. 22, 2016.
Examination Report for GB1321385.5, dated Jan. 25, 2017.
Supplementary European Search Report for EP11842166, completed on Jan. 18, 2017.
Fourth Office Action, Chinese Patent Application No. 201180025170X, dated Jun. 20, 2016.
GE Healthcare, Modular monitoring for critical care, iMM Solar 8000i and iMM Transport Pro Monitors, 2005.
GE Healthcare, Carescape Monitor B850, Engineered to help provide better care, 2009.
Office Action dated Jun. 23, 2017 for U.S. Appl. No. 13/300,526; (pp. 1-13).
Office Action dated Jun. 29, 2017 for U.S. Appl. No. 13/472,332; (pp. 1-23).
Office Action for Japanese Patent Application No. JP2014511465, dated Dec. 14, 2015.
Office Action for Japanese Patent Application No. JP2014511465, dated Nov. 4, 2016.
Examination Report for Australian Patent Application No. 2012255897, dated Nov. 4, 2015.
Office Action dated Aug. 23, 2017 for U.S. Appl. No. 13/895,270, pp. 1-10.
Office Action dated Sep. 21, 2017 for U.S. Appl. No. 14/289,833, pp. 1-8.
Exam Report for GB1310778.4, dated Dec. 1, 2016.
Exam Report for GB1310778.4, dated Feb. 24, 2017.
Rejection Decision, Chinese Patent Application No. 2012800351488, dated Apr. 28, 2017.
Third Office Action, Chinese Patent Application No. 2012800351488, dated Nov. 18, 2016.
Supplementary European Search Report for EP10823756, completed on Oct. 4, 2017.
Supplementary European Search Report for EP10824231, completed on Oct. 16, 2017.
Examination Report for GB1311848.4, dated Oct. 18, 2016.
Second Office Action for Chinese Patent Application No. CN2011800653708, dated Dec. 12, 2016.
Third Office Action for CN2011800655972, dated Jan. 2017.
Second Office Action for CN201380037855.5, dated Aug. 24, 2016.
Third Office Action for CN201380037855.5, dated May 12, 2017.
Anonymous: "Framebuffer—Wikipedia, the free encyclopedia", Mar. 14, 2010, XP055307861, Retrieved from the Internet: URL—https://en.wikipedia.org/w/index.php?title=Framebuffer&oldid=349748376 [retrieved on Oct. 5, 2016].
Supplementary European Search Report for EP11760006, completed on Oct. 5, 2016.
Examination Report for Australian Application No. 2013327128, dated Jan. 13, 2016.
Office Action for CA2887029, dated Apr. 8, 2017.
Office Action for CA2887029, dated May 2, 2016.
Search and Examination Report for GB1711443.0, dated Oct. 11, 2017.
Examination Report for GB1407581.6, dated May 17, 2017.
Patent Examination Report No. 1 for AU2013262812, dated Feb. 3, 2016.
"IntelliVue Patient Monitor MP20/30, MP40/50, MP60/70/80/90 Release G.0 with Software Revision G.0X.XX" Sep. 2008; See particularly pp. 3-19.
Examination Report for GB1421959.6, dated Jun. 16, 2017.
Office Action for JP2015512811, dated Apr. 3, 2017.
First Office Action for CN2013800376013, dated Nov. 15, 2016.
Office Action for JP2015512812, dated Feb. 20, 2017.

\* cited by examiner

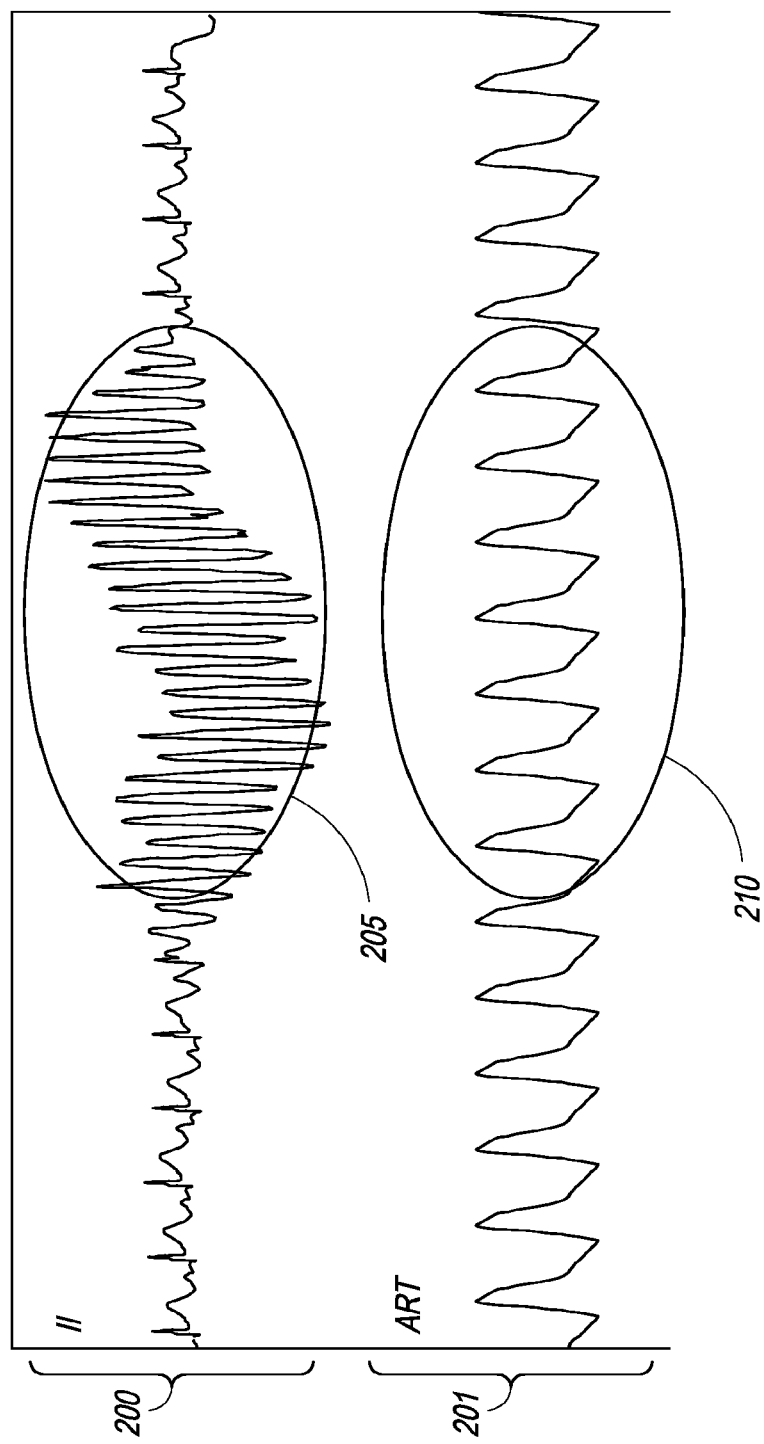

METHODS AND SYSTEMS TO DETERMINE MULTI-PARAMETER MANAGED ALARM HIERARCHY DURING PATIENT MONITORING

FIELD OF THE INVENTION

The present specification invention relates to patient monitoring systems. In particular, the specification discloses systems and methods for analyzing a plurality of physiological parameters to promote, demote, or suppress alarm conditions.

BACKGROUND OF THE INVENTION

Most patient monitoring is typically implemented by measuring and observing a plurality of physiological parameters such as: ECG (Electrocardiogram), Pulse Oximetry (involving measuring blood oxygen levels or $SpO_2$), Respiration (derived from ECG signal or from other parameters), Invasive Blood Pressure (or IBP that involves direct measurement of blood pressure from an indwelling catheter), and Non-Invasive Blood Pressure (or NIBP that involves use of automated oscillometric methods).

Typically these physiological parameters have a set of vital signs and derived measurements which can be configured to alert a caregiver if the measured values move outside of configured ranges. Each parameter has a plurality of alarms that can be considered to be of different priorities. However, prior art methods and systems tend to treat each of these parameters independently for deciding/determining alarm situations or fail to provide a workable mechanism for effectively determining whether an alarm state, derived from the signal of a particular patient monitoring device, is false, likely to be false, or sufficiently indicative of the state of a patient to warrant alerting a caregiver. As a result, the clinical user may experience an unacceptable number of alarms within these patient monitoring systems. The caregiver will ultimately see a conglomeration of alarm states from various fluctuations for each of the parameters, leading to unnecessary distraction and caregiver apathy regarding alarms.

Accordingly there is need in the art for methods and systems that effectively suppress or demote the number of false alarms the user sees and to make sure that when the system alarms there is a significant probability that the patient requires immediate attention.

SUMMARY OF THE INVENTION

In one embodiment, the present specification discloses a computer readable medium storing a plurality of programmatic instructions for processing data indicative of physiological parameters comprising: a) code for receiving ECG data generated at least in part by an ECG device, wherein said ECG data comprises a plurality of features and wherein at least one of said features has a designation associated therewith and a time of occurrence associated therewith; b) code for receiving pulse data indicative of a patient's pulse response, wherein said pulse data is obtained from at least one sensor separate from said ECG device and wherein said pulse data has a designation associated therewith and a time of occurrence associated therewith; c) code for correlating the designation and time of said at least one feature of the ECG data with the designation and time of the pulse data to determine a degree of correlation; and d) code for causing an alarm to issue, wherein the alarm is only issued if said degree of correlation indicates the patient has an abnormal heart condition.

Optionally, the plurality of programmatic instructions further comprises code for comparing said degree of correlation to a predetermined value. The code for causing an alarm to issue only causes the alarm to issue if said comparison indicates the patient has an abnormal heart condition. The designation of at least one feature of the ECG data is either normal or abnormal. The designation of the pulse data is either normal or abnormal. The correlation functions to determine if an abnormal feature in the ECG data is correlated in time with an abnormal pulse. If the correlation determines an abnormal feature in the ECG data is correlated in time with an abnormal pulse, an alarm indicative of an abnormal heart condition is issued. If not, an alarm is not issued or, if generated by another source, is actively suppressed. The correlation is further dependent upon at least one of an amplitude of an ECG signal, amplitude of a pulse signal, duration of a pulse signal, noise level within said ECG data, or noise level within said pulse data. The at least one sensor is an invasive blood pressure (IBP) monitoring device, a non-invasive blood pressure (NIBP) monitoring device, heart valve sounds monitoring device, or pulse oximetry ($SpO_2$) monitoring device. The plurality of instructions further comprises code for causing at least one sensor to initiate a collection of pulse data based on said ECG data. The code causes a non-invasive blood pressure monitoring device to inflate a cuff and collect pulse data when said ECG data is representative of a heart rhythm indicative of atrial fibrillation. The plurality of instructions further comprises code to cause a non-invasive blood pressure monitoring device to inflate a cuff and collect pulse data based upon said correlation.

In another embodiment, a computer readable medium storing a plurality of programmatic instructions for processing data indicative of physiological parameters comprising: a) code for receiving bio-impedance data generated at least in part by a respiration monitoring device, wherein said bio-impedance data comprises a plurality of features and wherein at least one of said features has a designation associated therewith and a time of occurrence associated therewith; b) code for receiving respiration data indicative of a patient's respiration, wherein said respiration data is obtained from at least one sensor separate from said respiration monitoring device and wherein said respiration data has a designation associated therewith and a time of occurrence associated therewith; c) code for correlating the designation and time of said at least one feature of the ECG data with the designation and time of the respiration data to determine a degree of correlation; and d) code for causing an alarm to issue, wherein the alarm is only issued if said degree of correlation indicates the patient has abnormal respiration.

Optionally, the respiration monitoring device is at least one of a capnography device, pneumatic respiration transducer device, strain gauge or stretch gauge. The sensor is at least one of an ECG device, invasive blood pressure (IBP) monitoring device, pulse oximetry ($SpO_2$) monitoring device, or motion detecting device. The motion detecting device is an accelerometer. The motion detecting device is an accelerometer integrated with an ECG electrode. The designation of at least one feature of the bio-impedance data is either normal or abnormal. The designation of the respiration data is either normal or abnormal. The correlation functions to determine if an abnormal feature in the bio-impedance data is correlated in time with abnormal respiration data. If said correlation determines an abnormal feature in the bio-impedance data is correlated in time with abnormal respiration data, an alarm indicative of an respiration condition is issued. The respiration condition is a sleep apnea event. The plurality of instructions further comprises code to receive motion data from said accelerometer and determine whether a patient has fallen. The plurality of instructions further comprises code to receive motion data from said accelerometer, to determine whether a patient is engaged in an activity which would increase the patient's respiration rate, and to cause said alarm to issue or not issue based, at least in part, on said determination. The plurality of instructions further comprises code to receive motion data from said accelerometer, to receive ECG data, to determine whether variations in ST segments of said ECG data are caused by patient activity, and to cause said alarm to issue or not issue based, at least in part, on said determination.

It should be appreciated that the plurality of instructions described herein are stored in a memory structure, such as a hard disk, ROM, RAM, or any other type of memory device, and executed by at least one processor. The instructions may be co-located with the sensors or monitors or may be remote therefrom. They may be integrated into a separate controller or computer that is in data communication with the sensors, or operated as a software module integrated into one or more of the sensing devices themselves.

BRIEF DESCRIPTION OF THE DRAWINGS

These and other features and advantages of the present invention will be appreciated, as they become better understood by reference to the following detailed description when considered in connection with the accompanying drawings, wherein:

FIG. 2a is a graphical representation of an ECG (III) signal with waveform noise and a corresponding IBP (ART) signal showing normal cardiac activity for the same interval;

DETAILED DESCRIPTION

Figure 1:
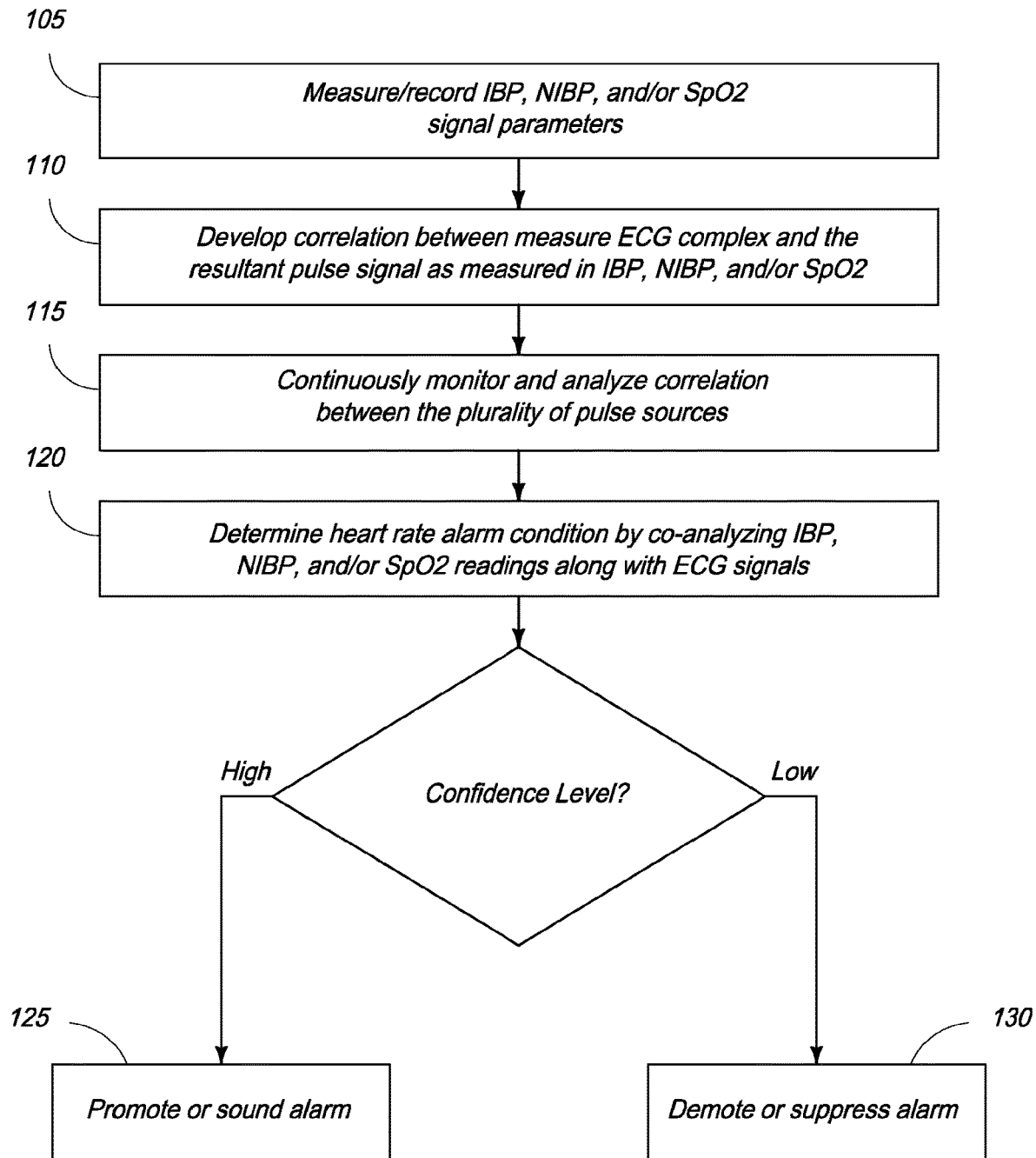
FIG. 1 shows a flow diagram depicting a method of using a plurality of parameters to determine an alarm hierarchy.

In one embodiment, the present specification discloses a system and method for collectively analyzing a plurality of physiological parameters and using the results to promote, demote, or suppress alarm notification. The present specification provides the benefits of producing more specific patient alarms and reducing the occurrence of false alarms, thereby permitting the monitoring personnel to perform more effectively.

In one embodiment, ECG parameters are considered with any one, or a combination of, the following sensor measurements: Invasive Blood Pressure (IBP); Non-Invasive Blood Pressure (NIBP); and, Blood Oxygen Level ($SpO_2$), such as via pulse oximetry. For each parameter there is a corresponding waveform signal that is created by measuring and sampling the signal off of a transducer.

For ECG, a waveform is derived from an electrical signal detected by cutaneously placed electrodes which respond to the propagation of electrical signals in heart muscles. In one embodiment, IBP uses an indwelling catheter with a transducer to create a voltage proportional to the pressure which results from the mechanical pumping action of the heart.

NIBP measurements are obtained via an external cuff coupled with an electronic pressure transducer. The cuff is automatically inflated and deflated at regular intervals to measure pressure oscillations. While NIBP is used to measure blood pressure, typically the pulse rate is also determined and reported as part of that process. For example, a caregiver may establish or set up a monitor to take an NIBP measurement every 15 minutes. This is typical in an operating room (OR) or in the post-anesthesia care unit (PACU) settings. Once every 15 minutes an NIBP measurement might report a value such as "120/80 (92) HR 77" (i.e. systolic pressure=120 mmHg, diastolic pressure=80 mmHg, mean arterial pressure=92 mmHg, and pulse rate=77 bpm). In this scenario, the NIBP parameter essentially provides an independent measure of pulse rate but only does so every 15 minutes.

In another embodiment, for purposes of the present specification, the cuff is inflated periodically, such as once every few minutes to a pressure adequate to measure the pulse rate. In one embodiment, the cuff is inflated to a diastolic pressure equal to or slightly greater than the most recently measured diastolic pressure. In another embodiment, the cuff is inflated to a mean arterial pressure equal to or slightly greater than the most recently measured mean arterial pressure. In another embodiment, the cuff is inflated so that both the diastolic pressure and mean arterial pressure are equal to or slightly greater than the most recently measured corresponding pressure. Pulses detected while the cuff is inflated are used as an alternate source of pulse information in the same way as described for IBP and $SpO_2$.

In yet another embodiment, NIBP is used to measure the strength and regularity of the pulse signal in addition to the pulse rate.

$SpO_2$ waveforms are derived by measuring variations in the amount of light detected by a photo-receptor after the light is shined through a patient's skin. The anatomical site used must have arterial blood flowing through it in sufficient quantity, such as, a fingertip or ear.

In any case, for each parameter, a signal is created which corresponds to either the electrical activity at the heart or the pumping action of the heart and its subsequent propagation into the periphery of the body. The individual parameters provide the caregiver with independent means of verifying agreement between results obtained via the electrical signal collected at the skin (ECG) and the mechanical response measured as pulse signals via invasive pressure lines (IBP), an external cuff (NIBP), or a pulse oximeter ($SpO_2$).

Further, when monitoring of the patient begins, each waveform is processed independently to produce a record of where each event (beat or pulse) occurs and to measure and record many parameters of each event. For each ECG event (i.e. heartbeat) the system measures and records the height and direction of the waveform deflections in multiple leads and records if the deflection pattern is typical and if it fell in the expected place in the sequence based on the previous events. In addition, other factors such as duration, rate of change, and locations of local minima and maxima within each lead are recorded. Ultimately, all recorded measurements are combined and compared to the previous beats and a diagnosis as to whether the beat is representative of "normal" or "abnormal" conduction is made.

For the purposes of the current specification, determining whether an alarm should be issued is a function of the time of occurrence of an ECG signal, (usually indexed off a prominent feature of the ECG waveform), whether the ECG signal designation is "normal" or "abnormal", and an estimate of the system's confidence in the beat's diagnosis. If the beat was normal in all measured parameters (closely matched preceding beats), occurred at the expected time, and all other measures of signal consistency and quality are high, the system will have high confidence that this signal is reliable, e.g. a confidence in excess of a predetermined threshold. All features measured by the ECG signal processing algorithm are reported to the signal correlation software module which then processes the data to generate the confidence level and compare the confidence level to a threshold. Similarly, other waveform parameters are recorded and reported (such as, but not limited to IBP, NIBP, and SpO2), including measurements for time of occurrence, amplitude, duration, peak change rates, and signal quality to the signal correlation software module.

Measured feature data from each parameter is combined using the signal correlation software module. In normal conditions, each electrical pulse, as measured by ECG, produces a pulse response which is also measured in the other parameters. Over time a relationship between time of occurrence, signal amplitude, pulse duration, noise level and confidence is created. When the signal quality is good, and each ECG complex is capturing a good mechanical response in the heart, and each of the other parameters is generating a good pulse response, the agreement or correlation between the each parameter is very high.

In one embodiment, when an abnormal beat (early or late, atrial or ventricular ectopic) is detected via ECG, there is a strong possibility of a reduced pulse response in one of the other parameters. If this ectopic beat occurs with some frequency, then a pattern is established between the ECG detecting "abnormal" conduction and the reduced pulse response in the other parameters. This pattern is recognized by the system as exhibiting a high confidence for representing a real event, thereby triggering an alarm.

In one embodiment, when the ECG signal is affected by noise (usually a result of patient movement) and an "abnormal" conduction is reported, the other parameters report normal pulse response. In this embodiment, the conduction is actually "normal" but the ECG signal is obscured by noise. The information from the other parameters (good and consistent pulse signal at the expected time with high confidence) is used to suppress any alarm or notification about the abnormal beat. The ECG then uses the information gathered from the other parameters to reconsider its diagnosis entirely. Similarly, the feedback from the pulse sources can help demote or suppress high and low pulse rate alarms and asystole alarms that are due to signal quality issues at the ECG electrodes. This is a result of having established a previous high correlation between the ECG and pulse sources. When the data from the pulse sources is of good quality and produces the expected results the system can suppress or demote the alarm from the ECG source.

Conversely, when an actual event occurs, such as an asystolic pause (the heart stops beating), the ECG will detect and report no activity and the pulse sources will detect and report no pulse responses. All these parameters together are producing signals which are closely correlated and suggest the heart has stopped. The system will then trigger an alarm with the highest urgency.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 shows a flow diagram depicting a method of analyzing a plurality of parameters to establish alarm hierarchy, in terms of the alarm's significance, thereby determining if an alarm is to be presented (via audio or visible signal) to a caregiver. In one embodiment of the multi-parameter alarm hierarchy method of the present invention, ECG parameters are considered in conjunction with IBP (Invasive Blood Pressure), NIBP (Non-Invasive Blood Pressure), and/or $SpO_2$ (Blood oxygen level, such as via pulse oximetry techniques) sensor measurements. To begin with, parameters such as the time of occurrence, signal strength, amplitude and regularity of every pulse signal, recorded by an IBP, NIBP, and/or $SpO_2$ sensor, are measured/recorded 105. Thereafter, at step 110 a one-to-one correlation is developed between each measured ECG complex and the resultant pulse signal as measured on IBP, NIBP, and/or $SpO_2$.

In step 115, the correlation between the pulse sources (that is, IBP, NIBP, and $SpO_2$ sensors) and the ECG signal is continuously monitored and analyzed. Heart rate alarm condition is determined, in step 120, after giving due consideration to the composite pulse rate readings from the IBP, NIBP, and/or $SpO_2$ sensors and the ECG to improve the overall level of confidence for an alarm situation. If the overall level of confidence is high, such as when parameters from multiple sources are in tandem, in step 125 an alarm is sounded or promoted. However, if the level of confidence is low, such as when parameters from relevant multiple sources are not in agreement with each other, then in step 130, the alarm is suppressed or demoted.

In one embodiment, for example, false ECG arrhythmia alarms are detected and suppressed, using the aforementioned method of the present invention, by simultaneously observing pulse signals from invasive pressure sensor, cuff pressure sensor, and/or the pulse oximeter and when adequate confidence in the pulse signal(s) allows the suppression of the ECG based alarm. Thus, if a sufficiently strong rhythmic pulse signal as measured on IBP, NIBP, and $SpO_2$ sensors is present, then there exists a reasonable certainty that the patient is not experiencing arrhythmia. In such example, an ECG alarm will be demoted or suppressed in the hierarchy of alarms to be sounded to a caregiver, in accordance with the method of the present invention, thereby avoiding false alarms related to arrhythmia conditions such as asystole, ventricular tachycardia, ventricular couplets and ventricular runs. Similarly, an ECG arrhythmia alarm is promoted if the condition is confirmed or corroborated by information form the pulse signal sources of IBP, NIBP, and/or $SpO_2$. For example, an ectopic beat will often create less pulse pressure and blood flow. This decreased peripheral pressure or flow can be detected on the $SpO_2$ signal, external cuff, and/or an arterial pressure line. The presence of the reduced signal in the $Spo_2$, cuff, and/or pressure lines confirms or increases the confidence to label those beats as ectopic beats.

Figure 2B:
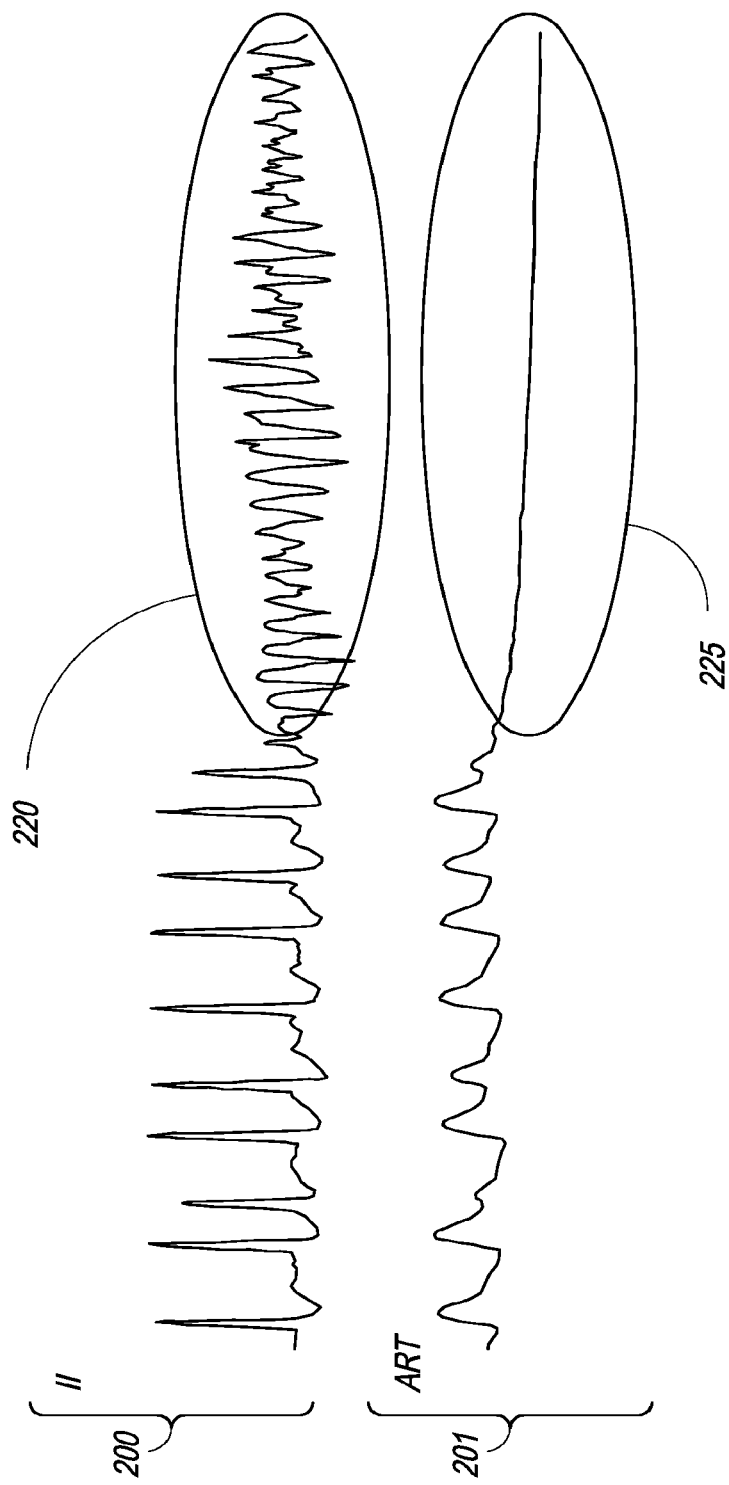
FIG. 2b is a graphical representation of an ECG (III) signal with waveform noise and a corresponding IBP (ART) signal showing lack of cardiac activity for the same interval.

FIG. 2a is a graphical representation of an ECG (III) signal 200 with waveform noise 205 and a corresponding IBP (ART) signal 201 showing normal cardiac activity 210 for the same interval. This figure shows an ECG waveform 200 with noise 205 closely resembling ventricular tachycardia, which would normally generate a high priority alarm. However, because the simultaneous IBP waveform 201 clearly shows continuing pulse with very regular rhythm and amplitude 210, this high priority alarm is demoted to a low priority alarm indicating "Noisy ECG". FIG. 2b is a graphical representation of an ECG (III) signal 202 with waveform noise 220 and a corresponding IBP (ART) signal 203 showing lack of cardiac activity 225 for the same interval. This figure shows an episode of ventricular tachycardia 220 which is confirmed by the cessation of pulsatile activity 225 in the invasive pressure waveform. Due to the great degree of correlation between the signals obtained from the two independent measurements, a high priority alarm is promoted.

Figure 3A:
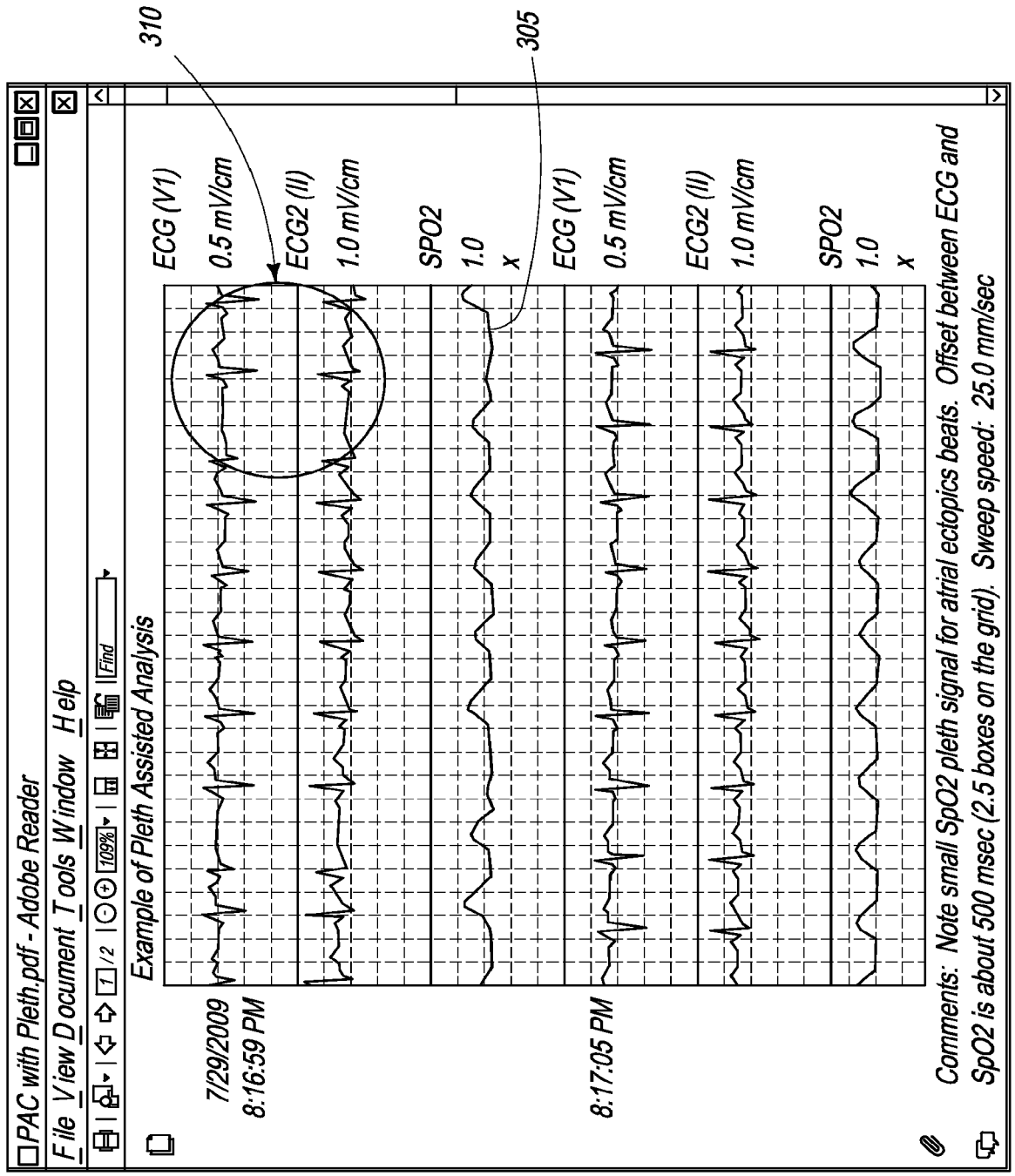
FIG. 3a is a graphical representation showing plethysmograph-assisted analysis for atrial ectopic beats.

FIG. 3a is a graphical representation showing plethysmograph-assisted analysis for atrial ectopic beats. As observable in the waveform of FIG. 3a, a weak $SpO_2$ plethysmograph signal 305 confirms ectopic beats 310 in the ECG waveform.

Figures 3B, 3C:
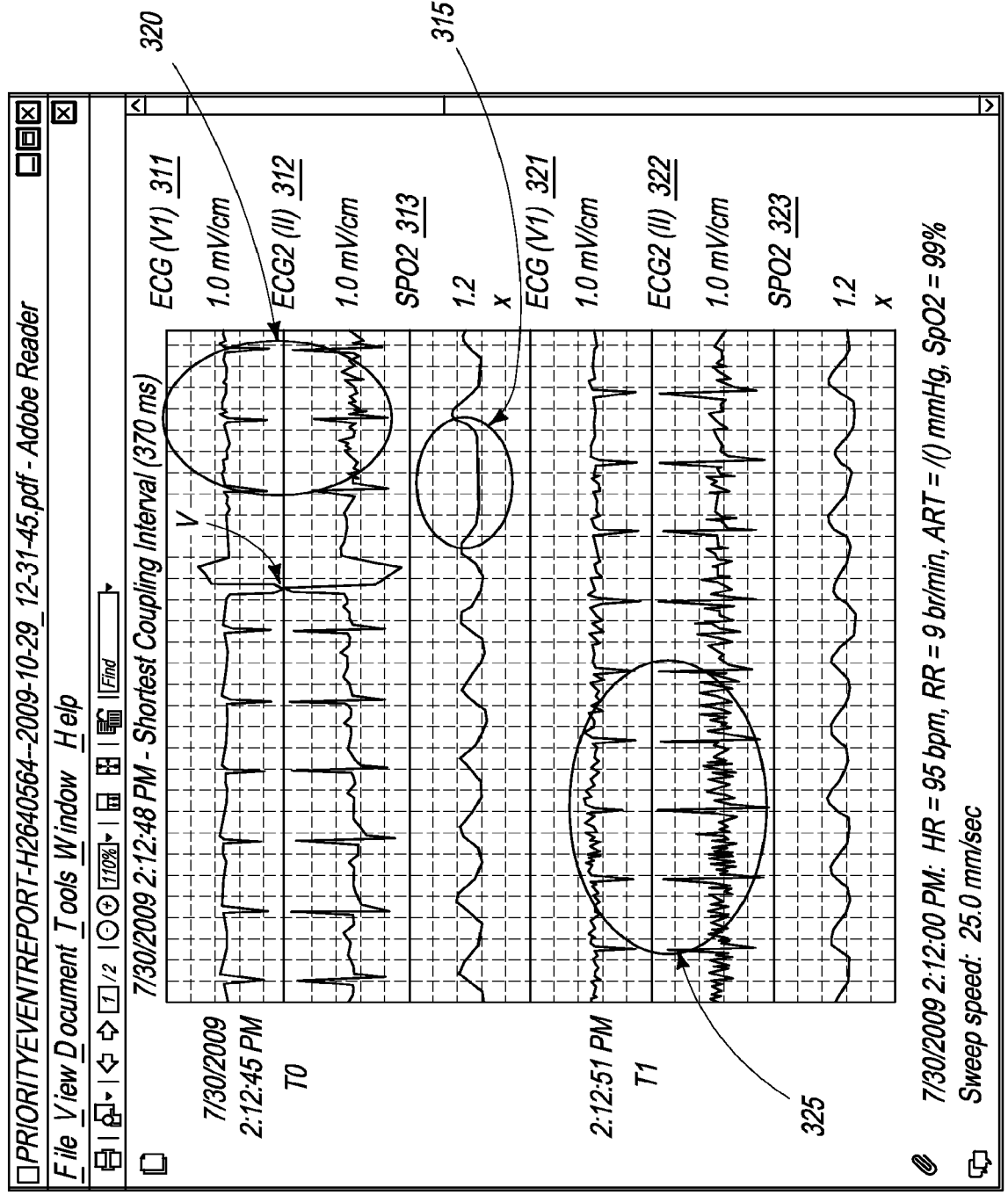
FIG. 3b is a graphical representation of ECG (V1), ECG2 (II) and $SpO_2$ signals at time $T_0$ for plethysmograph-assisted ventricular beat analysis.
FIG. 3c is a graphical representation of ECG (V1), ECG2 (II) and $SpO_2$ signals at time $T_1$ for plethysmograph-assisted ECG signal noise analysis.

FIG. 3b is a graphical representation of ECG (V1) 311, ECG2 (II) 312 and $SpO_2$ 313 signals at time $T_o$ for plethysmograph-assisted ventricular beat analysis and FIG. 3c is a graphical representation of ECG (V1) 321, ECG2 (II) 322 and $SpO_2$ 323 signals at time $T_1$ for plethysmograph-assisted ECG signal noise analysis. Now referring to FIG. 3b, the ventricular beat, V, is corroborated or confirmed in the $SpO_2$ graph 313 that correspondingly shows little or no signal response 315. This corroboration improves the overall confidence thereby promoting a heart rate alarm condition. However, as the ECG data gets noisy at the end of the strip 320, shown in FIG. 3b, and the beginning of the strip 325, shown in FIG. 3c, the correlated $SpO_2$ waveforms provide confirmation that none of the noise is likely a real beat. This allows for demotion or suppression of a heart rate alarm that would otherwise have been sounded if $SpO_2$ waveform was not considered and the ECG heart rate parameter were relied upon in isolation.

In another embodiment, a NIBP (Non-Invasive Blood Pressure) cuff is used as an alternative signal source in the same way as IBP and/or $SpO_2$, when necessary. The system will inflate the cuff periodically and also when the primary heart rate sources (ECG, IBP, $SpO_2$) are unavailable, in disagreement, or indicate a serious condition that needs to be verified. The system will perform periodic inflations and also on-demand inflation as described below.

For example, in one embodiment, a patient is monitored on NIBP and ECG only. The patient inadvertently removes some or all of their ECG electrodes such that the ECG parameter is effectively disabled. At this point the cuff inflates and begins "backup" monitoring of the pulse with NIBP. If the NIBP is producing a reasonable "in-bounds" pulse signal the system propagates a low-priority alarm to the caregiver ("Check ECG leads" or "Signal unavailable").

However, if the pulse rate is indicating an alarm condition (such as no pulse, high rate, low rate, or very different pulse strength or regularity than previously measured), the alarm message is elevated to a clinical alarm such as "ECG unavailable NIBP indicating pulse rate>120 bpm—Check Patient".

In another example, if an ECG analysis suggests a rhythm change to atrial fibrillation, the NIBP cuff on the patient is inflated in order to monitor the strength and regularity of the pulse measured in the NIBP cuff. This additional NIBP data is then used to confirm or suppress the atrial fibrillation diagnosis. Similarly, out of bounds heart rate alarms are checked via the NIBP cuff to confirm or deny rate violations before the alarm is sounded.

Persons of ordinary skill in the art should note that a plurality of other combinations of parameters can be utilized in accordance with the alarm hierarchy determination method of the present invention and that the use of parameters such as ECG, IBP, NIBP, and/or $SpO_2$ is only by way of a non-limiting example. However, it should be noted that the accurate suppression or promotion of an alarm requires the careful correlation of different physiological parameters to ensure that real events are being tracked and reported. It should also be noted herein that the occurrence of the ECG derived event is still reported as a notification or display to a patient monitor, but not as a clinical alarm, which is any visual or auditory signal designed to attract human attention and is indicative of an abnormal physiological state requiring immediate medical attention. This enables the caregiver to review excluded events from the multi-parameter analysis of the present invention.

According to another aspect of the present invention a plurality of physiological cross-parameters are also analyzed to determine alarm hierarchy. Persons of ordinary skill in the art would appreciate that a respiration signal can be derived from invasive blood pressure lines, depending on placement of a catheter, the hemodynamic condition of the patient, and the characteristics of respiration. In one embodiment, the invasive pressure line signal, observable as a pulse pressure variation which is driven by respiration, is used as a secondary respiration signal. Thus, the invasive pressure line signal is used in conjunction with a primary respiration signal source to confirm respiration rate changes or to identify apnea events.

Figure 4:
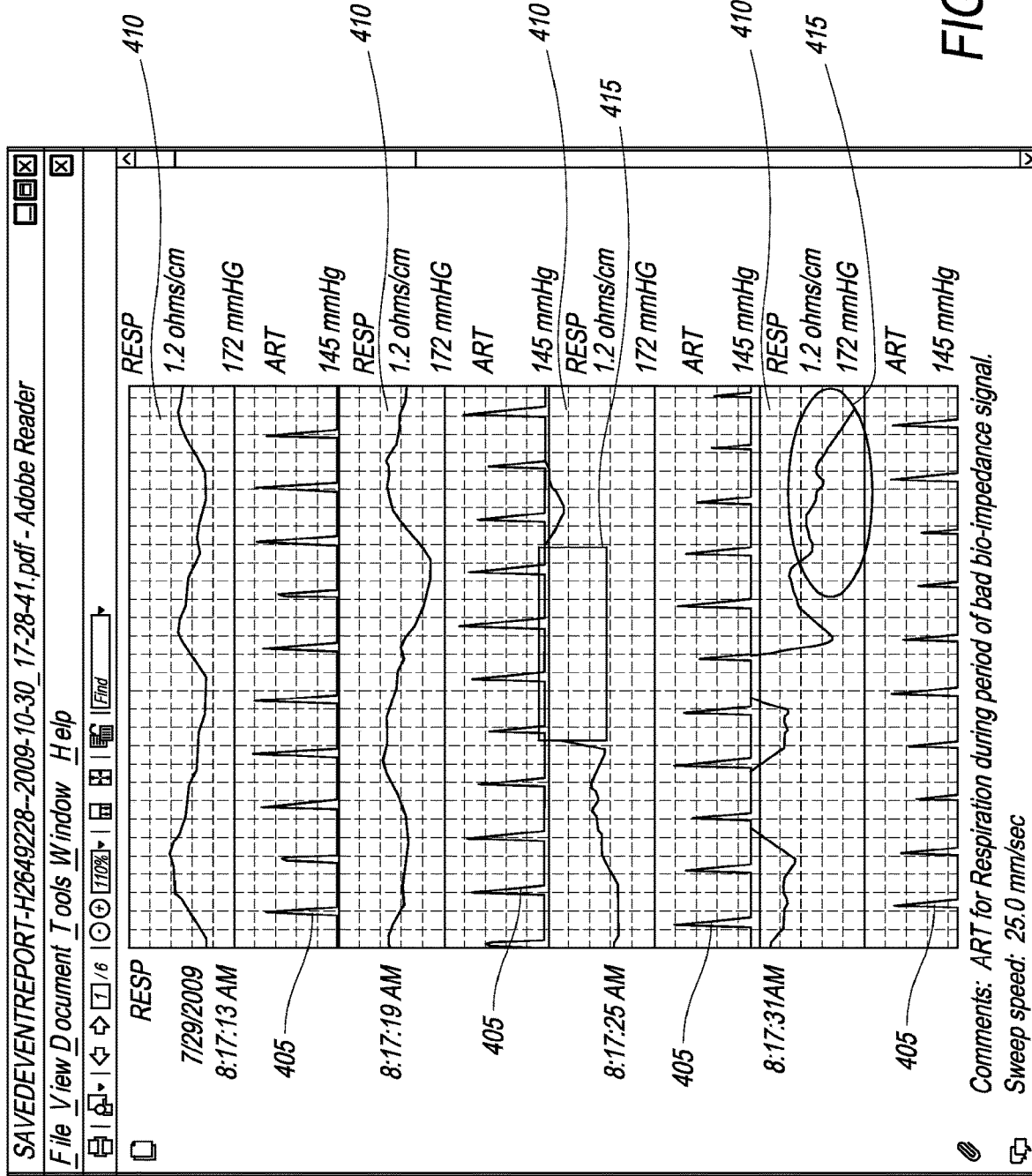
FIG. 4 is a graphical representation of invasive pressure systolic peak modulation with respiration signals.

FIG. 4 is a graphical representation of invasive pressure systolic peak modulation with respiration signals. Thus, FIG. 4 shows signal plots of how invasive pressure systolic peaks 405 modulate with respiration signals 410 in accordance with an embodiment of the present invention. This modulation is measured and used as a secondary source of respiration rate measurement. As observable in FIG. 4, the relationship between the bio-impedance respiration signal 410 and the invasive pressure signal 405 is established in the first six seconds. As the bio-impedance signal 410 degrades, at 415, the pressure signal 405 is used to establish the respiration rate even though the bio-impedance signal 410 is temporarily unavailable, thereby suppressing a false respiration rate related alarm. However, the fact that bio-impedance is unavailable is still reported as an event and not as a clinical alarm.

In one embodiment, a secondary respiration signal is derived by monitoring changes in the amplitudes of ECG signal, in multiple leads, during respiration cycle. These amplitude changes are a result of the heart moving in the chest relative to the measuring electrodes owing to movement of the chest and lungs during respiration. This, in turn, creates another pseudo-respiration signal that is used to confirm respiration changes when studied/analyzed in conjunction with a primary source of respiration signal, such as capnography, PRT (Pneumatic Respiration Transducer), a strain or a stretch gauge or any bio-impedance signal source known to persons of ordinary skill in the art. Since the pseudo-signal is not expected to be present and therefore reliable all the time (since in this embodiment the pseudo-signal depends on chest/lung movement), the pseudo-signal is used only when a high correlation is observed between the pseudo-signal and a primary respiration signal.

In another embodiment, a secondary respiration signal is derived by monitoring changes in the amplitudes of the SpO$_2$ plethysmograph or small changes in the oxygen saturation signal during the respiration cycle. These amplitude changes are a result of the heart moving in the chest owing to movement of the chest and lungs during respiration, thus creating another pseudo-respiration signal that is used to confirm respiration changes when studied/analyzed in conjunction with a primary source of respiration signal.

In one embodiment, motion signals from a motion detecting accelerometer are used as pseudo or secondary respiration signals in conjunction with a primary source of respiration signals. In one embodiment of the present invention, an accelerometer is integrated into an electrode wire snap thereby rendering the accelerometer virtually reusable with very low disposable cost.

Figure 5A:
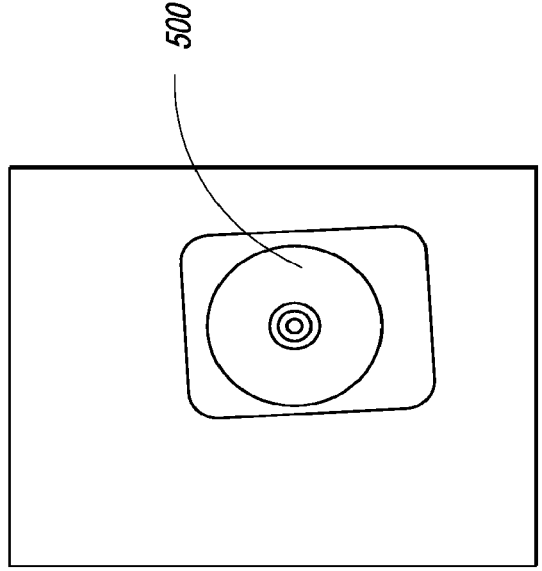
FIG. 5a is an illustration of one embodiment of a disposable ECG electrode.
Figure 5B:
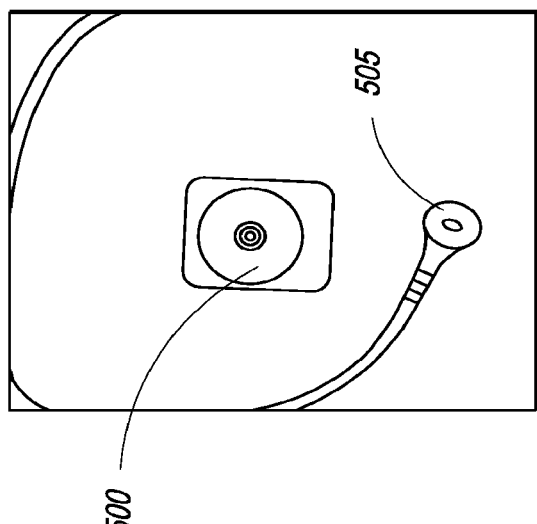
FIG. 5b is an illustration of the disposable ECG electrode shown in FIG. 4a, further showing a reusable snap electrode wire.

FIG. 5a is an illustration of one embodiment of a disposable ECG electrode while FIG. 5b is an illustration of the disposable ECG electrode shown in FIG. 5a further showing a reusable snap electrode wire.

Figure 5C:
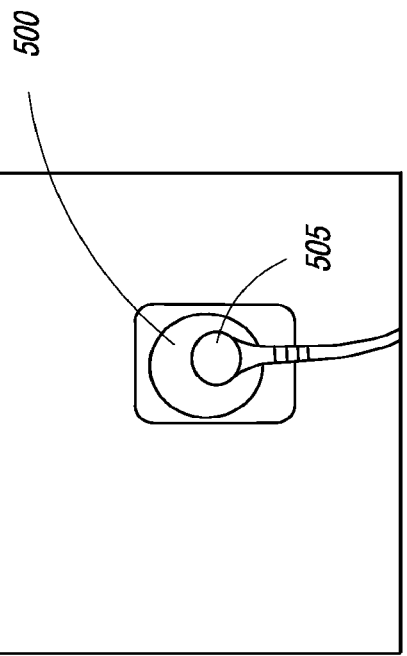
FIG. 5c is an illustration of the reusable snap electrode wire shown in FIG. 4b, attached to the ECG electrode and with an integrated accelerometer.

In one embodiment of the present invention, an accelerometer (not shown) is integrated into the electrode wire snap 505. In one embodiment, as shown in FIG. 5c, the electrode wire is attached to the ECG electrode 500. In one embodiment, a tri-axial accelerometer is used, such as, but not limited to, the ADXL330 3-axis iMEMS® accelerometer from Analog Devices. Persons of ordinary skill in the art should appreciate that the accelerometer can be integrated into other devices, apart from ECG electrodes, such as a cell-phone or other devices like the iPod™ from Apple™.

In one embodiment the spatial orientation of the accelerometer is maintained such that it is consistently applied in the same orientation relative to a patient. To enable this, mechanical fixtures such as locking snaps, tabs or adhesives are used to position, align and lock the accelerometer snap consistently into a position. In one embodiment, markings, such as a note saying "this end up", are placed on the electrode/accelerometer along with a locking tab or any other mechanical fixture to ensure that the accelerometer is always oriented the same way relative to the body and stays in this position. The accelerometer integrated ECG electrode is appropriately placed on a patient such that the position allows for maximized chest wall motion. Persons of ordinary skill in the art should appreciate that the accelerometer can be used as integrated with an ECG electrode and/or on a standalone basis. In one embodiment, two or more different 3-axis accelerometers are used and positioned in multiple locations on the patient's torso in order to maximize detection of measured quantities.

In situations where only the accelerometer signals are available while other primary respiration signals are unusable or unavailable—the accelerometer data is used as a proxy "dead-in-bed" detector which sounds an alarm when no movement or respiration signal is present. However, in situations where another source of primary respiration signal (such as bio impedance, stress or strain gauge, capnography) is available, the accelerometer signal is used to validate the primary respiration signal. Thus, when the accelerometer measurements are in agreement with other primary source(s) of measurement, there is increased confidence that the measured signal is correct and an alarm is sounded to the caregiver. However, data from the proxy accelerometer signal is used to suppress false alarms (for conditions such as low or high breath rate, apnea) from other respiration signal sources when the signal from the accelerometer indicates a different respiration signal with sufficiently high confidence. Thus, data from a plurality of sources is co-analyzed to produce a more robust measurement of respiration. This increases the quality of the respiration signal analysis and reduces unnecessary alarms for the caregiver.

According to one aspect of the present invention, motion signals from an accelerometer are used to determine and monitor patient posture. For example, the amount of time a patient spends in standing, sitting, active and/or supine positions is calculated and reported.

Figure 6:
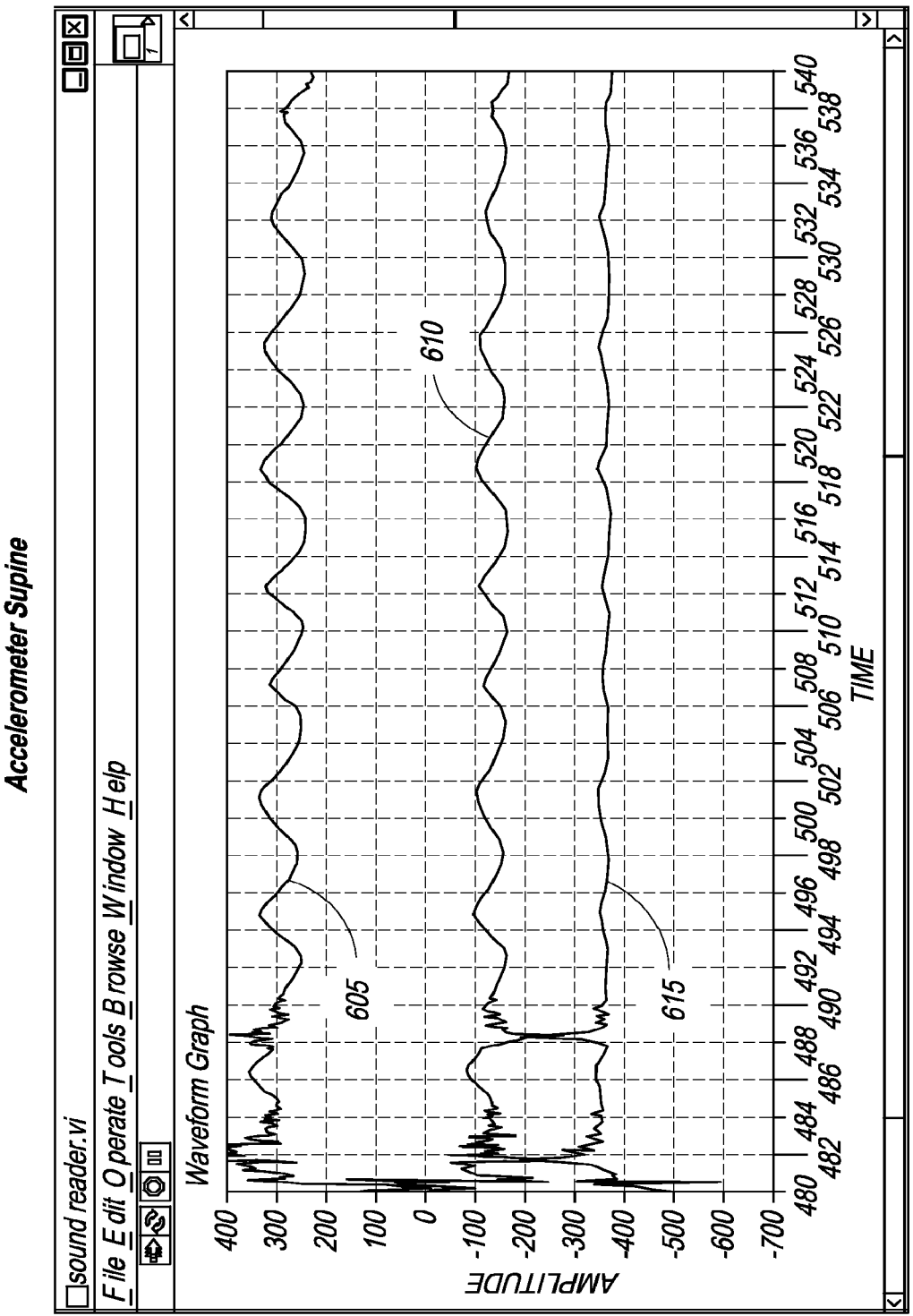
FIG. 6 is a graphical representation of chest wall movement in a patient wearing an accelerometer while supine.

FIG. 6 is a graphical representation of chest wall movement in a patient wearing an accelerometer while supine. A 3-axis accelerometer measures applied force in each of 3 different orthogonal directions. FIG. 6 depicts a graphical representation of the signal created by a chest worn accelerometer for a patient while lying down. The data represents 1 minute in time and shows the signal from each axis of the accelerometer. The effects of respiration can be seen in FIG. 6, particularly in waveform G 605 and waveform Y 610 and, to a lesser extent, in waveform B 615. Waveform G's 605 mean signal is about 300 counts, waveform Y's 610 is about −150 counts, and waveform B's 615 is −350 counts.

Figure 7:
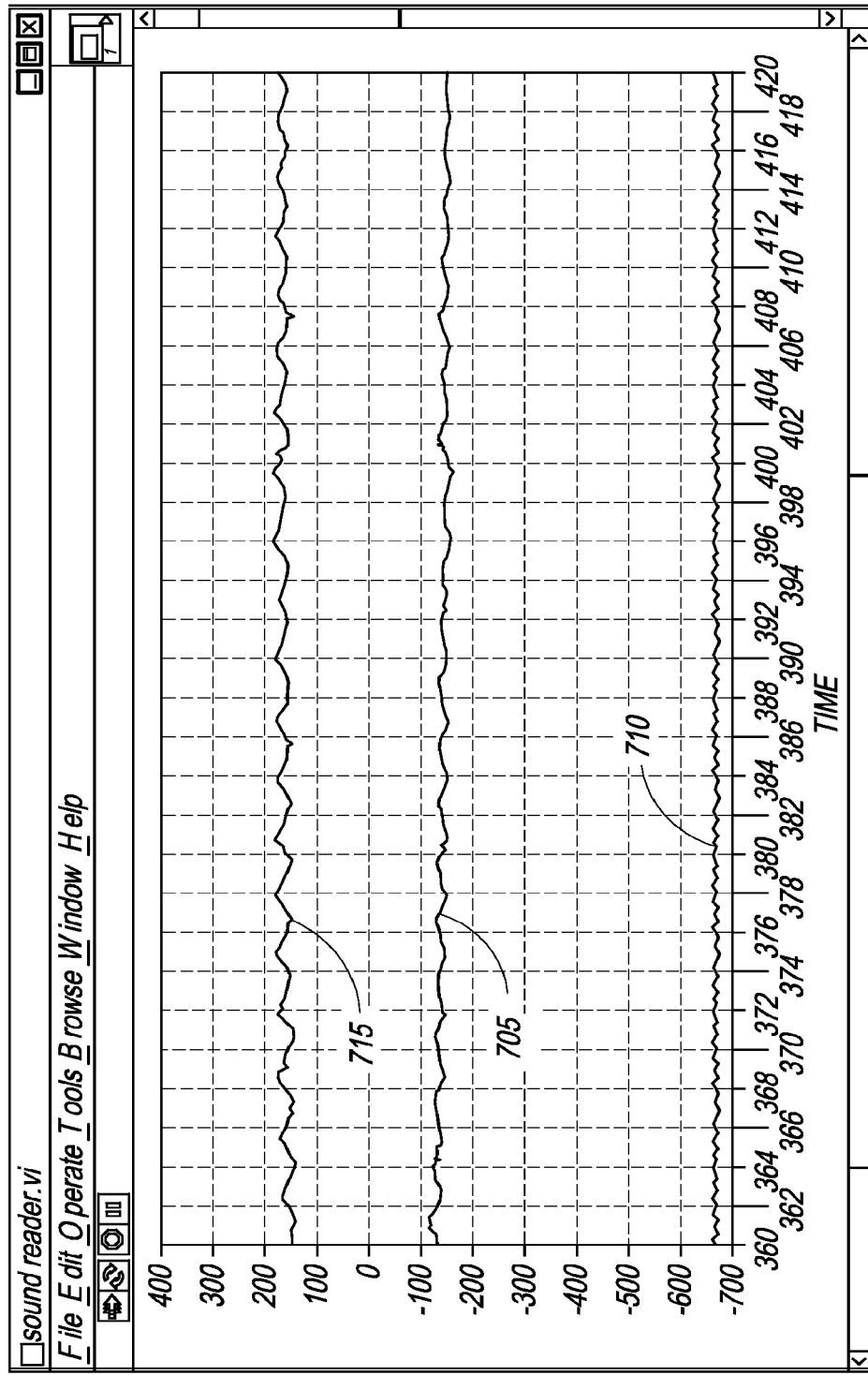
FIG. 7 is a graphical representation of chest wall movement in the same patient wearing an accelerometer after standing up.

FIG. 7 is a graphical representation of chest wall movement in the same patient wearing an accelerometer after standing up. The positional change of the patient thus results in dramatic changes in the mean levels of each signal. In comparison with a supine patient, waveform G's 705 mean level is now −130 counts, waveform Y's 710 is −650 counts, and waveform B's 715 is 150 counts. This effect is a result of the change in spatial orientation of the 3-axis accelerometer relative to the gravitational field of the earth. Provided that the accelerometer is attached to the patient in the same orientation each time, then the relative mean values of the signal off each axis will tell the clinician if the patient is "upright" (could be standing or sitting), supine, or perhaps partially propped up with pillows if between an upright and supine position.

This information is useful in assessing discharge decisions from a monitoring perspective. Similarly, sleep positions, such as on back, left side, right side, stomach, are monitored. In one embodiment, the number of position changes per hour is measured and quantified and used in conjunction with motion measurements from accelerometer to determine if a patients overall activity is what would be expected for a patient in a given state. For example, detection of lack of motion or posture change is notified to a caregiver as a need for the patient to be turned in bed to prevent bed sores.

In another embodiment, data collected by the accelerometer signifying position changes is used to detect falls and trigger alarm notification. For example, waveform signatures denoting a sudden change from a standing position to a supine position preceded by an impact would alert the system of a possible patient fall. The system would then promote or trigger an alarm notification.

According to another aspect of the present invention, apart from monitoring patient posture, accelerometer signals are also used to measure patient activity. In one embodiment, accelerometer signals are used to both count and record patient steps and patient step rates.

Figure 8:
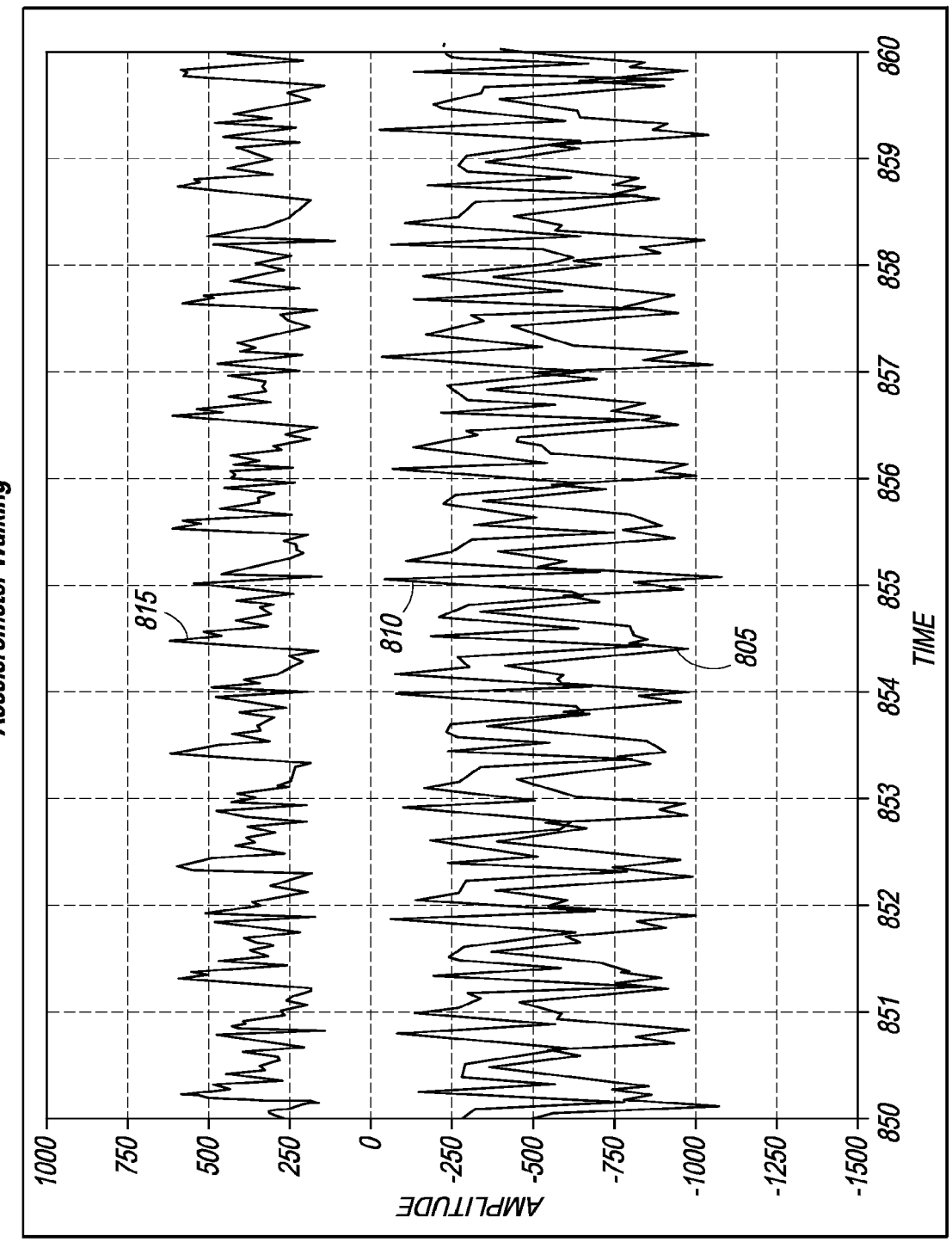
FIG. 8 is a graphical representation of chest wall movement in the same patient wearing an accelerometer while walking.

FIG. 8 is a graphical representation of chest wall movement in the same patient wearing an accelerometer while walking. The time axis represents 10 seconds of data collected while the patient was walking. The walking signature is quite different from the supine and standing signatures depicted in FIG. 6 and FIG. 7, respectively. The user can easily pick out each footfall (in waveform Y 810 and waveform G 805 in particular) and to see that in 10 seconds approximately 19 steps were taken. The actual steps could be measured by looking across all 3 bands for the characteristic rapid changes in each axis signal. These events can be counted (pedometer type function) and reported as a count or as a rate; for example, in this ten second time period, the event can be represented as 19 total steps or 114 steps per minute.

This information is used to calculate statistics such as the percentage of time the patient spends walking and at what step rates. Such statistics when analyzed in the long term over hours and days, in one embodiment, help in assessing ambulatory patients for parameters such as how much they are moving, how does their activity level compare to similar patients, whether or not they are candidates for discharge, and/or any other parameters as would be advantageously evident to persons of ordinary skill in the art.

According to another aspect of the present invention, the accelerometer signals are used to detect motion/activity artifacts induced signal changes in other physiological parameters being monitored for the patient. In one embodiment this is useful in suppressing or demoting an alarm situation during heightened patient activity. For example, respiration measurements by methods such as bio-impedance and pulse oximetry can be seriously compromised by patient gross motion. Persons of ordinary skill in the art would appreciate that ECG signal can be compromised by motion. To assess motion induced artifacts, an analysis of motion signal from the accelerometer is used to correlate specific noise in the ECG signal with specific patient motion activity, including walking Such sufficiently positive correlation enables false ECG alarms to be suppressed. In another embodiment use of accelerometer signals in conjunction with other physiological parameters enables improvement in the level of confidence for an alarm situation. For example, a possible marginal arrhythmia detected on the ECG which accompanied by a motion signal consistent with fainting is promoted to a higher alarm priority.

In another embodiment, changes in patient posture detected using the accelerometer is used to analyze and interpret measured changes in ECG ST Segment. It is well-known to those of ordinary skill in the art that the ST Segment is a portion of the ECG waveform which is monitored to identify ongoing myocardial infarction. Sometimes the ST Segment levels change with patient position as a result of the movement of the heart inside the chest relative to the ECG electrodes. ST segment changes due to position change are, however, not significant. Accelerometer signals provide necessary information conveying that positional changes preceded ST segment changes thereby enabling demotion of the alarm significance of an ST segment change.

According to one aspect of the present invention, motion signals from the accelerometer are used to modify overall sensitivity of the patient alarm system. In one embodiment, if the accelerometer signal analysis strongly suggests that the patient is walking or is very active the sensitivity of alarm system in the monitor is appropriately reduced. The objective here is to reduce false alarms that are induced by patient activity. According to another aspect of the present invention, patient activity level, monitored with accelerometer signals, is used to vary the need and kind of analysis that is performed on other physiological parameters. For example if the patient activity level is high due to activities such as walking or using a treadmill, then an ECG analysis for the patient is suspended during the period of the activity as ECG analysis requires high signal quality. Instead, in one embodiment, the overall sensitivity levels of the alarm system is pared down so that motion induced noise signals do not trigger false alarms while the some basic parameter analysis is continued.

According to a yet another aspect of the present invention, heart valve sounds are measured (such as by placing a microphone on the chest) to monitor mechanical activity of the heart to improve overall patient monitoring and also to reduce false alarms.

In one embodiment, heart valve sounds are used as a measure of patient pulse activity. The valve sounds from the heart form an independent pulse signal which is used to differentiate noise from signal at the ECG electrodes. As a first step, valve sound signature which matches each QRS location detected on an ECG is identified and recorded. In the next step, the quality of the recorded valve sound signals is determined based on parameters such as the strength, consistency, quality and regularity of the sound signal on a beat to beat basis. The determined sound quality measurement or signal to noise ratio is estimated on a continuous basis. The resultant valve sound quality is thereafter used to weigh how strongly the data from the sound channel (such as a microphone placed on the patient's chest) is used to promote or suppress alarm data from other physiological parameter measuring channels/sources such as ECG electrodes.

In another embodiment valve sounds from the heart form an independent pulse signal which are used to identify non-perfusing beats and pulseless electrical activity. It should be understood by persons of ordinary skill in the art that pulseless electrical activity is a general case of electromechanical disassociation in the heart. In some arrhythmia cases it is advantageous to identify beats for which there is no mechanical response. In other words, these beats are non-perfusing in that they have an electrical signal (probably abnormal) but do not cause the heart to pump. For example, there are cases in which pacemakers induce electrical signals in the heart which are detected by the ECG parameter, but which do not produce effective mechanical pumping. In this case, mechanical response, by way of valve sound signals measured on a beat by beat basis, in conjunction with ECG signals, enable identification of such events and alarm appropriately. For example, if an arrhythmia event detected at the ECG is verified by the valve sound signal there is an increased probability that this is a real event and would enable promoting this alarm due to the increased confidence in the correctness of the alarm. Such a scenario exists, for example, if the ECG analysis suggests a pause or asystole (no beats detected) and the heart valve sound signal also suggests no mechanical motion. This is a case of confirmed pause or asystole diagnosis and this alarm is promoted with confidence. Similarly, if an event is detected by the ECG but is not indicated by the heart valve sound signal, then the event alarm is suppressed or demoted. For example, the ECG signal may indicate a run of irregular beats that suggests a ventricular tachycardia. However, a high quality heart valve sound signal suggests that the pulse rate does not match the irregular beats that the ECG analysis is detecting. Therefore, in this case the alarm for the irregular beats is suppressed or demoted.

The invention claimed is:

1. A non-transitory computer readable medium configured to store a plurality of programmatic instructions for processing data indicative of physiological parameters comprising:
   code for receiving accelerometer data generated by an accelerometer device;
   code for analyzing the accelerometer data over a period of time, wherein the accelerometer data over the period of time is indicative of at least one of a number of steps taken by a wearer of the accelerometer device or a rate of the steps, and wherein the analyzed accelerometer data is indicative of a motion of the wearer;
   code for receiving physiological data generated by at least one physiological sensor used to monitor the wearer, wherein said physiological data has a time of occurrence associated therewith and wherein the physiological data comprises electrocardiogram (ECG) data and data indicative of the wearer's pulse signal;
   code for correlating the analyzed accelerometer data with the time of occurrence of the ECG data to determine a degree of correlation;
   code for causing an alarm to issue if the ECG data, which are correlated with the accelerometer data, is indicative of an abnormal physiological condition; and
   code for suppressing said alarm, which is based upon the ECG data, if the accelerometer data correlated with the ECG data is indicative of a regular motion of the wearer;
   code for suppressing said alarm if the ECG data comprises noise above a threshold value and the pulse signal is indicative of a normal state;
   code for increasing a priority level of the alarm if the ECG data comprises ectopic beats and the pulse signal is indicative of a lower than normal pulse rate; and
   code for increasing a priority level of the alarm if the ECG data is indicative of an asystolic pause and the pulse signal is not received.

2. The non-transitory computer readable medium of claim 1 wherein said plurality of programmatic instructions further comprises code for comparing said degree of correlation between the analyzed accelerometer data and the time of occurrence of the physiological data to a predetermined value.

3. The non-transitory computer readable medium of claim 1 wherein said code for correlating determines if an abnormal feature in the analyzed accelerometer data is correlated in time with the abnormal physiological condition.

4. The non-transitory computer readable medium of claim 1 wherein said degree of correlation is dependent upon at least one of the number of steps, the rate of steps, an amplitude of a physiological signal indicative of the physiological data, a duration of the physiological signal, or a noise level within the physiological data.

5. The non-transitory computer readable medium of claim 1 wherein the at least one physiological sensor comprises an ECG electrode.

6. The non-transitory computer readable medium of claim 1 further comprising code for modifying a sensitivity of an alarm.

7. The non-transitory computer readable medium of claim 6 wherein code for modifying the sensitivity of the alarm comprises code for reducing the sensitivity of the alarm if the analyzed accelerometer data is indicative of the regular motion of the wearer.

8. The non-transitory computer readable medium of claim 1 further comprises code for varying a correlation of the physiological data generated by the at least one physiological sensor.

9. The non-transitory computer readable medium of claim 1 further comprising code for suspending an operation of the at least one physiological sensor if the analyzed accelerometer data is indicative of the motion of the wearer.

10. The non-transitory computer readable medium of claim 1 further comprising code for analyzing the motion of the wearer using the analyzed accelerometer data to determine if the wearer is engaged in an activity causing an increase in the wearer's respiration rate and causing the alarm to issue based, at least in part, on said analysis.

11. The non-transitory computer readable medium of claim 1 wherein the accelerometer device is a tri-axial accelerometer.

12. The non-transitory computer readable medium of claim 11 wherein the accelerometer device is integrated with an ECG electrode attached to the wearer.

13. The non-transitory computer readable medium of claim 11 wherein the accelerometer device is integrated into an electrode wire snap of an ECG electrode.

14. The non-transitory computer readable medium of claim 1 further comprising code for causing the alarm to issue if the accelerometer data is indicative of cessation of all regular motion of the wearer or if the physiological data is unavailable.

15. The non-transitory computer readable medium of claim 1 further comprising code for analyzing the accelerometer data to determine a posture of the wearer and for recording changes in the posture.

16. The non-transitory computer readable medium of claim 15 further comprising code for causing the alarm to issue if a change in the wearer's posture is indicative of a fall.

17. The non-transitory computer readable medium of claim 16 further comprising code for causing a notification to issue if the overall activity state of the wearer does not lie with a predefined range.

18. The non-transitory computer readable medium of claim 15 further comprising code for determining a number of posture changes per hour and correlating the determined number with the accelerometer data to obtain an overall activity state of the wearer.

19. The non-transitory computer readable medium of claim 1 further comprising code for analyzing the accelerometer data to determine a posture of the wearer and for recording changes in the posture in relation to data obtained from the at least one physiological sensor, wherein the at least one physiological sensor comprises an ECG electrode.

20. The non-transitory computer readable medium of claim 1 further comprising code for detecting motion artifact induced signal changes in the physiological data using the accelerometer data.

21. The non-transitory computer readable medium of claim 1 wherein said plurality of programmatic instructions further comprises code for suppressing an alarm associated with a non-invasive blood pressure reading if the accelerometer data is indicative of physical activity greater than a threshold value.

22. The non-transitory computer readable medium of claim 1 further comprising code for suppressing an alarm by correlating the accelerometer data with one or more ECG waveforms.

23. The non-transitory computer readable medium of claim 1 further comprising code for increasing a priority level of the alarm if the physiological data is indicative of an arrhythmia and if the accelerometer data is indicative of a fainting by the wearer.

24. The non-transitory computer readable medium of claim 1 further comprising code for decreasing a priority level of the alarm if the physiological data is indicative of an ST segment change and if the accelerometer data is indicative of a positional change by the wearer.

* * * * *